US009181145B2

(12) United States Patent
Yilmaz et al.

(10) Patent No.: US 9,181,145 B2
(45) Date of Patent: Nov. 10, 2015

(54) PROCESS FOR THE ALKYLATION OF ORGANIC COMPOUNDS

(75) Inventors: Bilge Yilmaz, New York, NY (US); Ulrich Müller, Neustadt (DE); Faruk Özkirim, Ludwigshafen (DE); Dirk de Vos, Holsbeek (BE); Feng-Shou Xiao, Changchun (CN); Takashi Tatsumi, Kawasaki (JP); Xinhe Bao, Dalian (CN); Weiping Zhang, Dalian (CN); Hermann Gies, Sprockhövel (DE); Hiroyuki Imai, Tokyo (JP); Bart Tijsebaert, Sint-Andries (BE)

(73) Assignees: BASF SE, Ludwigshafen (DE); Tokyo Institute of Technology, Tokyo (JP)

( * ) Notice: Subject to any disclaimer, the term of this patent is extended or adjusted under 35 U.S.C. 154(b) by 165 days.

(21) Appl. No.: 13/438,408

(22) Filed: Apr. 3, 2012

(65) Prior Publication Data
US 2012/0259148 A1   Oct. 11, 2012

(30) Foreign Application Priority Data

Apr. 8, 2011 (WO) ................ PCT/CN2011/072556

(51) Int. Cl.
*C07C 2/66* (2006.01)
(52) U.S. Cl.
CPC ............... *C07C 2/66* (2013.01); *C07C 2529/70* (2013.01)
(58) Field of Classification Search
CPC ..... C07C 2/66; C07C 2529/70; B01J 29/7007
USPC ....................................................... 585/453
See application file for complete search history.

(56) References Cited

U.S. PATENT DOCUMENTS

| 5,139,759 A | 8/1992 | Cannan et al. |
| 5,453,554 A | 9/1995 | Cheng et al. |
| 5,962,759 A * | 10/1999 | Gajda ........................... 585/467 |
| 7,348,465 B2 | 3/2008 | Murray et al. |

(Continued)

FOREIGN PATENT DOCUMENTS

| CN | 101249968 | 8/2008 |
| WO | WO 2010/145077 | 12/2010 |
| WO | WO-2010146156 | 12/2010 |

OTHER PUBLICATIONS

PCT International Search Report in PCT/IB2012/051629, dated Aug. 30, 2012, 15 pgs.

(Continued)

*Primary Examiner* — In Suk Bullock
*Assistant Examiner* — Philip Louie
(74) *Attorney, Agent, or Firm* — Servilla Whitney LLC

(57) ABSTRACT

The present invention relates to a process for the alkylation of an organic compound comprising: (a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element, (b) contacting the catalyst with one or more alkylatable organic compounds in the presence of one or more alkylating agents in one or more reactors for obtaining one or more alkylated organic compounds, wherein the one or more zeolitic materials is obtainable from a synthetic process which does not employ an organotemplate as structure directing agent.

22 Claims, 3 Drawing Sheets

(56) References Cited

U.S. PATENT DOCUMENTS

| | | | |
|---|---|---|---|
| 7,569,739 B2 | 8/2009 | Dandekar et al. | |
| 2003/0204121 A1* | 10/2003 | Miller | 585/467 |
| 2010/0322847 A1* | 12/2010 | Xiao et al. | 423/709 |

OTHER PUBLICATIONS

Bellussi, G. et al., "Liquid-Phase Alkylation of Benzene with Light Olefins Catalyzed by β Zeolites", *Journal of Catalysis*, vol. 157 1995, pp. 227-234.

Halgeri, Anand B. et al., "Novel catalytic aspects of beta zeolite for alkyl aromatics transformation", *Applied Catalysis A: General*, vol. 181 1999, pp. 347-354.

Majano, Gerardo et al., "Al-Rich Zeolite Beta by Seeding in the Absence of Organic Template", *Chem. Mater.*, vol. 21, No. 18 2009, pp. 4184-4191.

Tang, Xiang-Hai et al., "Tert-butylation of phenol over Hβ, HY, HZSM-5 and HAIMCM-41", *Zeolites to Porous MOF Materials—the 40th Anniversary of International Zeolite Conference* 2007, pp. 1454-1459.

Xie, Bin et al., "Organotemplate-Free and Fast Route for Synthesizing Beta Zeolite", *Chemistry of Materials*, vol. 20, No. 14 2008, pp. 4533-4535.

Yoon, Ji W. et al., "Trimerization of isobutene over a zeolite beta catalyst", *Journal of Catalysis*, vol. 245 2007, pp. 253-256.

\* cited by examiner

PROCESS FOR THE ALKYLATION OF ORGANIC COMPOUNDS

CROSS-REFERENCE TO RELATED APPLICATIONS

This application claims the benefit of priority 35 U.S.C. §365(c) of PCT application number PCT/CN2011/072556, filed on Apr. 8, 2011, which is incorporated herein by reference in its entirety.

TECHNICAL FIELD

The present invention relates to a process for the alkylation of an organic compound as well as to the use of a catalyst comprising a zeolitic material having a BEA framework structure in an alkylation reaction, wherein the zeolitic material is obtainable from a synthetic process which does not employ an organotemplate as structure directing agent.

BACKGROUND

Alkylation processes and, in particular, processes for the alkylation of aromatics are of considerable importance on the industrial scale for the production of basic chemicals. Thus, the alkylation of benzene with ethylene and propylene to produce ethylbenzene and cumene is for example widely used in the petrochemical industry. In this respect, cumene is an important chemical intermediate mainly used for the production of phenol and acetone, whereas ethylbenzene is an intermediate used in the production of styrene. In addition to these, long chain alkylbenzenes are useful as lubricant base stocks and as intermediates in the production of detergents.

For the production of such basic chemicals Lewis and Bronsted acids are typically used, such that a variety of zeolites are commonly employed as alkylation catalysts. Thus, alkylation of aromatic hydrocarbon compounds employing certain crystalline zeolite catalysts is known in the art. In this respect, alkylation of benzene with ethylene and propylene in the presence of zeolite catalysts represents the preferred commercial techniques for the production of ethylbenzene and cumene.

However, along with the desired monoalkylated products, typical alkylation processes produce di- and tri-alkylated products, in addition to oligomers and other side-products. As a result of this, time and cost intensive separation processes must normally be employed for obtaining an alkylation product which is sufficiently pure to be used as a feed in the production of the follow-up products.

Accordingly, considerable efforts have been made for developing processes and catalysts affording higher selectivities for the monoalkylation products in order to increase the effectiveness of the known industrial processes.

In this respect, U.S. Pat. No. 7,569,739 B2 for example relates to aromatics alkylation, and in particular to the alkylation of benzene with ethylene and propylene to produce ethylbenzene and cumene, respectively. Furthermore, said document is concerned with the alkylation of aromatics with long chain alkylating agents to produce the corresponding long chain alkylbenzenes. In the alkylation reactions, zeolitic materials, and in particular zeolitic materials having the MWW framework structure are used. In particular, relates to a means of enhancing the selectivity of the alkylation reaction towards monoalkylated products by modifying the zeolitic materials with phosphorous.

U.S. Pat. No. 7,348,465 B2 specifically relates to the alkylation of benzene with propylene and butenes, especially for the production of feedstocks used for producing follow-up chemicals such as cumene and s-butylbenzene. In particular, said document aims at providing a method for enhancing the selectivity of aromatic alkylation to monoalkylated species. To this effect, the use of molar blends of propylene and one or more linear butenes are taught therein. A clear drawback to said method, however, resides in the fact that it is highly limited both with respect to the alkylatable organic compounds and to the alkylating agents which may used therein, in addition to the fact that only mixtures of monoalkylated products may be obtained.

In Bellussi et al., Journal of Catalysis 1995, 157, pp. 227-234, the activity and selectivity of various zeolites including zeolite Beta in the alkylation of benzene catalyzed by the former is discussed, in particular with respect to the respective reactions of ethylene and propylene with benzene. In this respect, Bellussi et al. report on an increase in both the conversion rate and the selectivity of zeolite Beta in said alkylation reaction with decreasing Si/Al molar ratio of the zeolite Beta used therein. However, as may be taken from the results disclosed in said document, the moderate increase in selectivity for the monoalkylated species with descreasing Si/Al molar ratio of the zeolite Beta materials is accompanied by a comparatively greater increase in di- and trialkylation products. The corresponding observation is almade in Halgeri et al., Applied Catalysis A: General 1999, 181, pp. 347-354, wherein the effect of dealumination of zeolite Beta on its activity and selectivity in the alkylation of aromatics is discussed. In particular, regarding the selectivity of zeolite Beta towards dialkylation products in the reaction of benzene with isopropanol, the results displayed in said document show a decrease in said selectivity with increasing dealumination of the zeolite Beta material used in the reaction.

Finally, regarding further alkylation reactions catalyzed by zeolite Beta, Yoon et al., Journal of Catalysis 2006, 245, pp. 253-256, for example relates to the trimerization of isobutene over a zeolite Beta catalyst. Tang et al. in "From Zeolites to Porous MOF Materials—the $40^{th}$ Anniversary of International Zeolite Conference", Studies in Surface Science and Catalysis 2007, pp. 1454-1459, on the other hand, concerns the tert-butylation of phenol over zeolitic materials including H-zeolite Beta.

There however remains a need to improve the selectivity of alkylation reactions, in particular in view of a time and cost-effective method for providing high purity feedstocks of a wide variety of basic chemicals employed in large scale industrial production processes.

SUMMARY

Embodiments of the present invention are directed to a process for the alkylation of an organic compound comprising (a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element, (b) contacting the catalyst with one or more alkylatable organic compounds in the presence of one or more alkylating agents in one or more reactors for obtaining one or more alkylated organic compounds, wherein the one or more zeolitic materials is obtainable from a synthetic process which does not employ an organotemplate as structure directing agent.

In one or more embodiments the one or more zeolitic materials are non-calcined. Y can be selected from the group consisting of Si, Sn, Ti, Zr, Ge, and combinations of two or more thereof. The Y:X molar ratio of one or more of the one or more zeolitic materials can be in the range of from 1 to 50.

In one or more embodiments, one or more of the one or more zeolitic materials comprises one or more alkali metals M. The molar ratio of M:X can range from 0.01 to 20. At least a portion of the alkali metal atoms M can be substituted by one or more cations and/or cationic elements.

In one or more embodiments, the BET surface area determined according to DIN 66135 of one or more of the one or more zeolitic materials ranges from 150 to 650 m$^2$/g. The one or more zeolitic materials can comprise zeolite Beta.

In one or more embodiments, the one or more alkylatable organic compounds comprises one or more alkylatable aromatic compounds, wherein one or more of the one or more alkylatable aromatic compounds is optionally substituted with one or more functional groups. The one or more alkylatable aromatic compounds can comprise one or more aromatic compounds selected from the group consisting of substituted or unsubstituted benzene, naphthalene, anthracene, naphthacene, perylene, coronene, phenanthrene, and heteroaromatic derivatives thereof. The one or more functional groups can comprise one or more functionalities selected from the group consisting of linear or branched alkyl, aryl, alkaryl, alkoxy, aryloxy, cycloalkyl, halide, and derivatives thereof.

In one or more embodiments, the one or more alkylating agents comprise one or more compounds selected from the group consisting of olefins, alcohols, aldehydes, alkyl halides, and derivatives thereof. The olefins can comprise one or more alkenes.

In a specific embodiment, the one or more alkylatable organic compounds comprise one or more organic compounds selected from the group consisting of substituted or unsubstituted benzene, toluene, and heteroaromatic derivatives thereof, and wherein the one or more alkylating agents comprises one or more olefins selected from the group consisting of ethene, propene, butane and derivatives thereof.

In one or more embodiments, the molar ratio of the one or more alkylatable organic compounds to the one or more alkylating agents ranges from 0.1:1 to 50:1.

In a specific embodiment, step (b) is conducted at a temperature ranging from 100 to 350° C. Step (b) can be conducted at a pressure comprised in the range of from 0.2 to 250 bar. Step (b) can be conducted for a duration of from 0.5 to 100 h.

In one or more embodiments, the process of the invention is a continuous process. The one or more reactors can contain the catalyst in the form of a fixed bed and/or as a fluidized bed. The catalyst comprising one or more zeolitic materials having a BEA framework structure can be provided in the form of a molding.

Other embodiments of the present invention are directed to a method comprising the step of contacting one or more chemical compounds with a catalyst comprising one or more zeolitic materials having a BEA framework structure for catalyzing an alkylation reaction including one or more alkylatable organic compounds and one or more alkylating agents as the reagents, wherein the one or more zeolitic materials are obtainable from a synthetic process which does not employ an organotemplate as structure directing agent.

DETAILED DESCRIPTION

Accordingly, present invention provides an improved process for the alkylation of organic compounds. Thus, it has surprisingly been found that such processes involving the use of a catalyst comprising zeolitic materials having a BEA framework structure, and in particular zeolite Beta, may be considerably improved by using a zeolitic material therein which is obtainable from a synthetic process which does not employ an organotemplate as structure directing agent. In particular, it has quite unexpectedly been found that by using such a zeolite material, the selectivity of the alkylation process may be considerably improved, especially with respect to the monoalkylated products. More specifically, it has quite surprisingly been found that the amount of polyalkylated products, and in particular of di- and trialkylated products may be considerably be reduced, especially in reactions involving the alkylation of aromatics. Furthermore and quite unexpectedly, it has been found that also with respect to the regioselectivity of such alkylation reactions, the use of a zeolitic material obtainable from an organotemplate-free synthetic process affords results which may not be achieved using conventional zeolitic materials obtained from organotemplate mediated synthetic methodologies.

In addition to these unexpected results, it has surprisingly been found that the use of a catalyst comprising such zeolitic materials in alkylation reactions affords a tremendously improved kinetic control thereof, as a result of which by way of example a greatly increased regioselectivity may be achieved in alkylation reactions. Thus, it has for example unexpectedly been found that a far higher regioselectivity may be achieved using such zeolitic materials in an alkylation catalyst for the alkylation of aromatics and in particular of subsitituted benzenes, wherein the ortho-, meta-, and/or para-positions may be preferably alkylated. This highly unexpected behavior may very well be linked to the further highly unexpected finding, wherein alkylation processes involving the use of such a catalyst comprising zeolitic materials having a BEA framework structure which is obtainable from a synthetic process which does not employ an organotemplate as structure directing agent display a greatly reduced transalkylation activity compare to commercial zeolitic materials having a BEA framework which are obtained using organotemplates.

Thus, the present invention concerns a process for the alkylation of an organic compound comprising:
(a) providing a catalyst comprising one or more zeolitic materials having a BEA framework structure, wherein the BEA framework structure comprises YO$_2$ and optionally comprises X$_2$O$_3$, wherein Y is a tetravalent element, and X is a trivalent element,
(b) contacting the catalyst with one or more alkylatable organic compounds in the presence of one or more alkylating agents in one or more reactors for obtaining one or more alkylated organic compounds,
wherein the one or more zeolitic materials are obtainable from a synthetic process which does not employ an organotemplate as structure directing agent.

According to the present invention, there is no particular restriction as to the number and/or types of zeolitic materials which are provided as a catalyst in step (a) of the inventive process, provided that the have the BEA framework structure and at least comprise YO$_2$, and provided that they are suited for catalyzing the alkylation of an organic compound as defined in the respective embodiments and/or specific embodiments of the present invention. Thus, by way of example, the one or more zeolitic materials may comprise one or more zeolites selected from the group consisting of zeolite Beta, [B—Si—O]-BEA, [Ga—Si—O]-BEA, [Ti—Si—O]-BEA, Al-rich beta, CIT-6, tschernichite, and pure silica beta, wherein the one or more zeolitic materials comprise zeolite Beta. Again, among the zeolite Beta comprised in the one or more zeolitic materials, there is no particular restriction as to which specific type thereof may be used, provided that it is obtainable from a synthetic process which does not employ an organotemplate.

Thus, according to one or more embodiments of the present invention, the one or more zeolitic materials provided as a catalyst in step (a) comprise zeolite Beta.

In principle, the one or more zeolitic materials having a BEA framework structure which are employed in the inventive process may be obtained by any conceivable synthetic process, provided that it may equally be obtained from a process which does not employ an organotemplate as structure directing agent. The one or more zeolitic materials having a BEA framework structure are obtained from a synthetic process which does not employ an organotemplate as structure directing agent. In Xiao et al., Chem. Mater. 2008, 20, pp. 4533-4535 and Supporting Information, for example, a process for the synthesis of zeolite Beta is described, in which crystallization of an aluminosilicate gel is conducted using zeolite Beta seed crystals. In this respect, WO 2010/146156 A may also be mentioned, which relates to organotemplate-free synthesis of zeolitic materials having the BEA framework structure, and in particular to the organotemplate-free synthesis of zeolite Beta. In Majano et al., Chem. Mater. 2009, 21, pp. 4184-4191, on the other hand, Al-rich zeolite Beta materials having Si/Al ratios as low as 3.9 are discussed which may be obtained from reactions employing seeding in the absence of organic templates.

According to one or more embodiments the present invention, the one or more zeolitic materials provided as a catalyst in step (a) do not contain more than an impurity of an organic structure directing agent typically used in the synthesis of zeolitic materials having a BEA framework structure, in particular specific tetraalkylammonium salts and/or related organotemplates such as tetraethylammonium and/or dibenzylmethylammonium salts, and dibenzyl-1,4-diazabicyclo[2,2,2]octane. Such an impurity can, for example, be caused by organic structure directing agents still present in seed crystals used in the synthetic process.

Furthermore, in one or more embodiments, the one or more zeolitic materials, are non-calcined, meaning that they have note been subject to a calcination step. Within the meaning of the present invention, a calcination step generally designates a process involving the heating of the one or more zeolitic materials above a temperature of 500° C. More preferably, however, a non-calcined zeolitic material according to the present invention designates a material not having been subject to a temperature exceeding 450° C., more preferably 350° C., more preferably 300° C., more preferably 250° C., more preferably 200° C., and even more preferably not exceeding 150° C. In general, a calcination step may designate any step which may be employed in the synthesis of the one or more zeolitic materials used in the inventive process. According to one or more embodiments of the present invention, however, a calcination step only refers to a step conducted after completion of the crystallization of the one or more zeolitic materials having a BEA framework structure from one or more precursor compounds which do not have a BEA framework structure, with the exception of any seeding crystals which may be employed therein. According to a specific embodiment of the present invention, a calcination step only refers to a step which is normally or suitably performed after completed crystallization of the one or more zeolitic materials for the removal of organotemplates from the framework structure.

Thus, according to one or more embodiments of the present invention, the one or more zeolitic materials provided as a catalyst in step (a) of the inventive process are non-calcined.

Within the meaning of the present invention, $YO_2$ and optionally $X_2O_3$ comprised in the BEA framework structure of the one or more zeolitic materials are contained therein as structure building elements, as opposed to non-framework elements which can be present in the pores and cavities formed by the framework structure and typical for zeolitic materials in general.

According to the present invention, Y comprised in the one or more zeolitic materials having a BEA framework structure stands for any conceivable tetravalent element, wherein Y is one or more tetravalent elements. In one or more embodiments, tetravalent elements include Si, Sn, Ti, Zr, and Ge, and combinations thereof. More preferably, Y stands for Si, Ti, or Zr, or any combination of said trivalent elements, even more preferably for Si and/or Sn. In a specific embodiment, Y stands for Si.

Thus, according to one or more embodiments of the present invention, Y comprised in the one or more zeolitic materials provided as a catalyst in step (a) is selected from the group consisting of Si, Sn, Ti, Zr, Ge, and combinations of two or more thereof, Y preferably being Si.

In one or more embodiments of the present invention, the framework of the one or more zeolitic materials having a BEA structure further comprises $X_2O_3$, wherein X stands for any conceivable trivalent element, wherein X is one or more trivalent elements. In one or more embodiments, trivalent elements include Al, B, In, and Ga, and combinations thereof. More preferably, Y stands for Al, B, or In, or any combination of said trivalent elements, even more preferably for Al and/or B. According to the present invention, it is particularly preferred that X stands for Al.

Thus, according to one or more embodiments of the present invention, X optionally comprised in the one or more zeolitic materials provided as a catalyst in step (a) is selected from the group consisting of Al, B, In, Ga, and combinations of two or more thereof, X preferably being Al.

According to one or more embodiments of the present invention, the one or more zeolitic materials having a BEA framework structure provided as a catalyst in step (a) comprise $X_2O_3$ in addition to $YO_2$. In principle, with respect to said one or more embodiments, there is no particular restriction as to the Y:X molar ratio displayed by the one or more zeolitic materials such that in principle zeolitic materials having any conceivable and realizable Y:X molar ratio may be used. Thus, by way of example, the one or more zeolitic materials may display Y:X molar ratios ranging anywhere from 1 to 50, wherein preferably the Y:X molar ratio is comprised in the range of from 2 to 35, more preferably of from 2.5 to 25, more preferably of from 3 to 15, more preferably of from 3.5 to 10, and even more preferably in the range of from 4 to 8. According to specific embodiments, the Y:X molar ratio of the one or more zeolitic materials provided as a catalyst in step (a) is comprised in the range of from 4 to 6.

Thus, according to one or more embodiments of the present invention, wherein X is comprised in the one or more zeolitic materials provided as a catalyst in step (a), the Y:X molar ratio thereof is in the range of from 1 to 50, preferably of from 2 to 35, more preferably of from 2.5 to 25, more preferably of from 3 to 15, more preferably of from 3.5 to 10, more preferably of from 4 to 8, and even more preferably in the range of from 4 to 6.

In one or more embodiments, the one or more zeolitic materials comprise one or more alkali metals M, wherein the one or more alkali metals are selected from the group consisting of Li, Na, and K, wherein, specifically, the one or more alkali metals are sodium and/or potassium, and even more preferably sodium. Therefore, in a specific embodiment, the one or more alkali metals M preferably comprised in the one or more zeolitic materials provided as a catalyst in step (a) is selected from the group consisting of Li, Na, and K, wherein more preferably the one or more alkali metals M comprise Na and/or K, more preferably Na, and wherein even more preferably M is Na.

According to one or more embodiments of the present invention wherein the one or more zeolitic materials provided as a catalyst in step (a) comprise one or more alkali metals M, there is no general restriction as to the amount of the one or more alkali metals contained therein. Thus, in embodiments of the inventive process wherein the one or more zeolitic materials provided as a catalyst in step (a) additionally comprise $X_2O_3$, the molar ratio M:X of the one or more alkali metals to the one or more trivalent elements X may by example range anywhere from 0.01 to 20, wherein it is preferred that the M:X ratio be comprised in the range of from 0.05 to 10, more preferably of from 0.1 to 5, more preferably of from 0.5 to 2, more preferably of from 0.7 to 1.5, more preferably of from 0.9 to 1.3, and even more preferably of from 1 to 1.2. According to specific embodiments of the present invention, the molar ratio M:X displayed by the one or more zeolitic materials used in step (a) is comprised in the range of from 1 to 1.1.

Thus, according to one or more embodiments of the present invention wherein the one or more zeolitic materials provided as a catalyst in step (a) comprises $X_2O_3$ and one or more alkali metals M, the molar ratio of M:X preferably ranges from 0.01 to 20, more preferably from 0.05 to 10, more preferably from 0.1 to 5, more preferably from 0.5 to 2, more preferably from 0.7 to 1.5, more preferably from 0.9 to 1.3, more preferably from 1 to 1.2, and even more preferably from 1 to 1.1.

In general, at least a portion of the one or more alkali metals M comprised in the one or more zeolitic materials provided as a catalyst in step (a) can be substituted by one or more cations and/or cationic elements suited for ion-exchange in the zeolitic material, with the exception of organotemplates specifically used in the synthesis of zeolitic materials having a BEA framework structure, in particular specific tetraalkylammonium salts and/or related organotemplates such as tetraethylammonium and/or dibenzylmethylammonium salts and/or dibenzyl-1,4-diazabicyclo[2,2,2]octane. Apart from organotemplates, however, there is no general restriction according to the present invention as to the one or more cations and/or cationic elements by which at least a portion of the one or more alkali metals M may be substituted, provided that the one or more substituted zeolitic materials provided as a catalyst in step (a) are suited for catalyzing the alkylation of an organic compound. According to specific embodiments, the one or more cations and/or cationic elements are selected from the group consisting of $H^+$, $NH_4^+$, lithium, potassium, calcium, magnesium, barium, transition metals, and combinations thereof, wherein preferably the one or more cations and/or cationic elements are selected from the group consisting of $H^+$, $NH_4^+$, lithium, potassium, calcium, magnesium, barium, lanthanum, cerium, nickel, platinum, palladium, and combinations thereof, wherein more preferably at least a portion of the one or more alkali metal atoms M in said specific embodiments is exchanged with $H^+$ and/or $NH_4^+$, and even more preferably with $H^+$.

With respect to the substitution of the one or more alkali metals M in the preferred one or more zeolitic materials obtainable, and preferably obtained from a synthetic process which does not employ an organotemplate as structure directing agent, there is no particular restriction as to the method according to which the substitution is achieved, wherein it is preferred according to the present invention that the substitution is achieved by ion-exchange. According to the present invention, the term "ion-exchange" generally refers to non-framework ionic elements and/or molecules contained in the one or more zeolitic materials. In general, any conceivable ion-exchange procedure with all possible ionic elements and/or molecules can be conducted on the zeolitic material, with the exception of organic structure directing agents specifically used in the synthesis of zeolitic materials having a BEA framework structure, in particular specific tetraalkylammonium salts and/or related organotemplates such as tetraethylammonium and/or dibenzylmethyl ammonium salts and/or dibenzyl-1,4-diazabicyclo[2,2,2]octane.

Therefore, According to specific embodiments of the present invention, at least a portion of the one or more alkali metal atoms M preferably contained in the one or more zeolitic materials provided as a catalyst in step (a) is substituted by one or more cations and/or cationic elements, wherein the one or more cations and/or cationic elements preferably comprise one or more cations and/or cationic elements selected from the group consisting of $H^+$, $NH_4^+$, lithium, potassium, calcium, magnesium, barium, transition metals, and combinations thereof, more preferably from the group consisting of $H^+$, $NH_4^+$, lithium, potassium, calcium, magnesium, barium, lanthanum, cerium, nickel, platinum, palladium, and combinations thereof, wherein even more preferably at least a portion of the alkali metal atoms M is exchanged with $H^+$ and/or $NH_4^+$, preferably with $H^+$, wherein the substituted catalyst is preferably obtainable by ion-exchange.

According to the present invention, there is no particular restriction as to the crystalline structure of the one or more zeolitic materials provided as a catalyst in step (a) of the inventive process, provided that these display a BEA framework structure, and, in particular, that the one or more zeolitic materials afford an X-ray diffraction pattern comprising the reflections typical of a BEA framework structure. Within the meaning of the present invention, an X-ray pattern typical of a BEA framework structure primarily designates a pattern of reflections comprised in an x-ray diffractogramm, wherein the 2θ diffraction angles are typical of a BEA framework structure, and wherein preferably also the relative intensities of the individual reflections are typical of a BEA framework structure. According to specific embodiments of the present invention, the one or more zeolitic materials having a BEA framework structure display an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern.

More preferably, the one or more zeolitic materials having a BEA framework structure display an X-ray diffraction pattern comprising at least the following reflections:

| Intensity (%) | Diffraction angle 2θ/° [Cu K(alpha 1)] |
|---|---|
| [9-29] | [21.11-21.21] |
| 100 | [22.16-22.26] |
| [10-30] | [25.06-25.16] |
| [8-28] | [26.82-26.92] |
| [12-32] | [28.43-28.53] |
| [27-47] | [29.27-29.37] |
| [7-27] | [30.04-30.14] |
| [9-29] | [33.00-33.10] |
| [11-31] | [43.01-43.11] | wherein 100% relates to the intensity of the maximum peak in the X-ray powder diffraction pattern.

According to a specific embodiment, the one or more zeolitic materials having a BEA framework structure provided as a catalyst in step (a) of the inventive process display an X-ray diffraction pattern comprising at least the following reflections:

wherein more preferably the X-ray diffraction pattern comprises at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [6-26] | [25.54-25.74] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein more preferably the X-ray diffraction pattern comprises at least the following reflections:

| Intensity (%) | Diffraction angle 2θ/° [Cu K(alpha 1)] |
|---|---|
| [9-29] | [21.11-21.21] |
| 100 | [22.16-22.26] |
| [10-30] | [25.06-25.16] |
| [6-26] | [25.59-25.69] |
| [8-28] | [26.82-26.92] |
| [12-32] | [28.43-28.53] |
| [27-47] | [29.27-29.37] |
| [7-27] | [30.04-30.14] |
| [9-29] | [33.00-33.10] |
| [11-31] | [43.01-43.11] | wherein 100% relates to the intensity of the maximum peak in the X-ray powder diffraction pattern.

Thus, According to specific embodiments of the present invention, the one or more zeolitic materials provided as a catalyst in step (a) has an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern, wherein even more preferably the X-ray diffraction pattern further comprises the following reflection:

| Intensity (%) | Diffraction angle 2θ/° [Cu K(alpha 1)] |
|---|---|
| [6-26] | [25.54-25.74] |

According to the present invention, there is no particular restriction as to the surface area of the one or more zeolitic materials provided as a catalyst in step (a) of the inventive process provided that the one or more zeolitic materials are suitable for catalyzing the alkylation of an organic compound. Thus, with respect to the BET surface area of the one or more zeolitic materials determined according to DIN 66135, by way of example these may from 200 to 550 m²/g, wherein preferably the BET surface area is comprised in the range of from 230 to 500 m²/g, more preferably of from 250 to 450 m²/g, more preferably of from 270 to 400 m²/g, and even more preferably of from 280 to 340 m²/g. According to specific embodiments, the BET surface area determined according to DIN 66135 ranges from 290 to 320 m²/g.

According to specific embodiments of the present invention, the one or more zeolitic materials provided as a catalyst in step (a) are obtainable, and preferably obtained, according to a synthetic process for the organotemplate-free synthesis of a zeolitic material having a BEA framework structure, wherein said synthetic process comprises the steps of (1) preparing a mixture comprising seed crystals and one or more sources for $YO_2$; and (2) crystallizing the mixture;

wherein when the BEA framework preferably comprises $X_2O_3$, the mixture according to step (1) further comprises one or more sources for $X_2O_3$.

According to said synthesis for providing the one or more zeolitic materials in step (a), at no point does the mixture provided in step (1) and crystallized in step (2) contain more than an impurity of an organic structure directing agent specifically used in the synthesis of the one or more zeolitic materials having a BEA framework structure, in particular specific tetraalkylammonium salts and/or related organotemplates such as tetraethylammonium and/or dibenzylmethylammonium salts, and dibenzyl-1,4-diazabicyclo[2,2,2]octane. Such an impurity can, for example, be caused by organic structure directing agents still present in seed crystals used in the synthesis. Organotemplates contained in seed crystal material may not, however, participate in the crystallization process since they are trapped within the seed crystal framework and therefore may not act structure directing agents within the meaning of the present invention.

According to the present invention, a zeolitic material having a BEA framework structure is crystallized in step (2) of the synthetic method. For this purpose, $YO_2$ can be provided in step (1) in any conceivable form, provided that a zeolitic material having a BEA framework structure comprising $YO_2$ can be crystallized in step (2). Preferably, $YO_2$ is provided as such and/or as a compound which comprises $YO_2$ as a chemical moiety and/or as a compound which (partly or entirely) is chemically transformed to $YO_2$ during the inventive process. In one or more embodiments of the present invention, wherein Y stands for Si or for a combination of Si with one or more further tetravalent elements, the source for $SiO_2$ provided in step (1) can be any conceivable source. There can therefore be used, for example, all types of silica and silicates, preferably fumed silica, silica hydrosols, reactive amorphous solid silicas, silica gel, silicic acid, water glass, sodium metasilicate hydrate, sesquisilicate or disilicate, colloidal silica, pyrogenic silica, silicic acid esters, or tetraalkoxysilanes, or mixtures of at least two of these compounds.

According to one or more embodiments of the synthetic method, wherein the mixture according to step (1) comprises one or more sources for $SiO_2$, said source preferably comprises one or more compounds selected from the group consisting of silica and silicates, preferably silicates, more preferably alkali metal silicates. Among the preferred alkali metal silicates, the one or more sources comprise water glass, more preferably sodium and/or potassium silicate, and more preferably sodium silicate. In specific embodiments of the present invention, the source for $SiO_2$ is sodium silicate. Furthermore, in embodiments comprising silica, fumed silica is preferred.

According to one or more embodiments of the present invention, wherein the one or more zeolitic materials having a BEA framework structure comprise $X_2O_3$, one or more sources for $X_2O_3$ are provided in step (1) of the synthetic method. In general, $X_2O_3$ can be provided in any conceivable form, provided that a zeolitic material having a BEA framework structure comprising $X_2O_3$ can be crystallized in step (2). In one or more embodiments, $X_2O_3$ is provided as such and/or as a compound which comprises $X_2O_3$ as a chemical moiety and/or as a compound which (partly or entirely) is chemically transformed to $X_2O_3$ during the inventive process.

According to one or more embodiments of the synthetic method, wherein X stands for Al or for a combination of Al with one or more further trivalent elements, the source for $Al_2O_3$ provided in step (1) can be any conceivable source. There can be used for example any type of alumina and aluminates, aluminum salts such as, for example, alkali metal aluminates, aluminum alcoholates, such as, for example, aluminum triisopropylate, or hydrated alumina such as, for example, alumina trihydrate, or mixtures thereof. In one or more embodiments, the source for $Al_2O_3$ comprises one or more compounds selected from the group consisting of alumina and aluminates, preferably aluminates, more preferably alkali metal aluminates. Among the preferred alkali metal aluminates, the one or more sources preferably comprises sodium and/or potassium aluminate, more preferably sodium aluminate. In specific embodiments of the synthetic method, the source for $Al_2O_3$ is sodium aluminate.

In cases wherein the mixture of step (1) further comprises one or more sources for $X_2O_3$ including one or more boron compounds, for example free boric acid and/or borates and/or boric esters, such as, for example, triethyl borate or trimethyl borate, can be used as starting materials.

According to specific embodiments of the synthetic method, the mixture according to step (1) comprises one or more silicates as a source for $YO_2$ and one or more aluminates as a source for $X_2O_3$, more preferably one or more alkali metal silicates and/or one or more alkali metal aluminates, and even more preferably one or more water glass compounds and/or one or more alkali metal aluminates, wherein the alkali metal of said specific embodiments preferably comprises sodium and/or potassium, more preferably sodium, and wherein the alkali metal even more preferably is sodium.

In one or more embodiments of the synthetic method, wherein the mixture according to step (1) comprises one or more sources for $X_2O_3$, the $YO_2:X_2O_3$ molar ratio of the mixture can have any conceivable value, provided that a zeolitic material having a BEA framework structure comprising both $YO_2$ and $X_2O_3$ is crystallized in step (2). Generally, the molar ratio ranges from 1 to 100, preferably from 5 to 85, more preferably from 10 to 60, more preferably from 20 to 55, more preferably from 25 to 50, more preferably from 35 to 45, and particularly preferably from 38 to 42.

In specific embodiments of the synthetic method, the zeolitic material obtained and/or obtainable and/or the inventive material as such according to the synthetic method comprises one or more alkali metals M, preferably sodium and/or potassium, and more preferably sodium. The alkali metal can be added at any conceivable stage of the synthetic method, wherein preferably it is also added in step (1). More preferably, the entire quantity of the alkali metal comprised in the zeolitic material having a BEA framework structure is added in step (1) of the synthetic method. In specific embodiments of the synthetic method, the alkali metal is partly or entirely contained in the one or more sources for $YO_2$ and/or $X_2O_3$ provided in step (1), wherein the alkali metal is partly provided by a further source. According to said specific embodiments wherein the one or more alkali metals M are partly provided by one or more further sources, there is no general restriction as to which type of source may be used, provided that a zeolitic material having a BEA framework structure is obtained which as such and/or after having been subject to a step of at least partly substituting the one or more alkali metals M contained therein is suitable for catalyzing the alkylation of an organic compound. In one or more embodiments the one or more further sources for providing one or more of the one or more alkali metals comprises one or more alkali metal halides, and or one or more alkali metal hydroxides, wherein the halides are selected from the group consisting of fluoride, chloride, and bromide. According to specific embodiments of the synthetic method, the one or more further sources comprise one or more alkali metal hydroxides, preferably sodium and/or potassium hydroxide, and even more preferably sodium hydroxide.

In general, the alkali metal M can be contained in the mixture according to step (1) of the synthetic method in any conceivable amount, provided that a zeolitic material having a BEA framework structure is crystallized in step (2). In one or more embodiments, the $M:YO_2$ molar ratio in the mixture according to step (1) ranges from 0.1 to 2, more preferably from 0.2 to 1.5, more preferably from 0.3 to 1.2, more preferably from 0.4 to 1, more preferably from 0.5 to 0.9, more preferably from 0.55 to 0.8, and more preferably from 0.6 to 0.75. According to specific embodiments of the synthetic method, the $M:YO_2$ molar ratio in the mixture according to step (1) ranges from 0.65 to 0.7.

According to one or more embodiments of the synthetic method, the mixture according to step (1) comprises one or more sources for $X_2O_3$ and one or more alkali metals M. In general, any conceivable amounts of these components can be contained in the mixture provided that a zeolitic material having a BEA framework structure is crystallized in step (2). In one or more embodiments, the $YO_2:X_2O_3:M$ molar ratios in the mixture according to step (1) range from (1-100):1:(2-90), more preferably from (5-85):1:(5-70), more preferably from (10-60):1:(8-50), more preferably from (20-55):1:(13-35), more preferably from (25-50):1:(15-30), more preferably from (35-45):1:(20-29), and even more preferably from (38-42):1:(25-28).

According to one or more embodiments of the synthetic method for obtaining the one or more zeolitic materials having a BEA framework structure, the mixture provided in step (1) can contain one or more sources for hydroxide anions $OH^-$. In general any conceivable source for $OH^-$ can be used, wherein the one or more sources preferably comprises a metal hydroxide, more preferably a hydroxide of an alkali metal M, more preferably sodium and/or potassium hydroxide, and even more preferably sodium hydroxide.

In general the $OH^-:YO_2$ molar ratio of the mixture according to step (1) of the synthetic method can have any conceivable value, provided that a zeolitic material having a BEA framework structure is crystallized in step (2). In one or more embodiments, said molar ratio is comprised in the range of from 0.1 to 1, more preferably of from 0.4 to 0.65, more preferably of from 0.43 to 0.62, more preferably from 0.57 to 0.6, and even more preferably from 0.55 to 0.61.

According to specific embodiments of the synthetic method, seed crystals are provided in step (1), wherein said seed crystals comprise a zeolitic material having a BEA framework structure. In general, said seed crystals can comprise any zeolitic material having a BEA framework structure, provided that a zeolitic material having a BEA framework structure is crystallized in step (2). In one or more embodiments, the zeolitic material having a BEA framework structure comprised in the seed crystals is a zeolitic material which is obtainable and preferably obtained according to the synthetic method. In a specific embodiment, the zeolitic material having a BEA framework structure comprised in the seed crystals is the same as the zeolitic material having a BEA framework structure which is then crystallized in step (2). Particularly preferred are seed crystals comprising zeolite Beta, more preferably zeolite Beta which is obtainable or has preferably been obtained according to the synthetic method. In specific embodiments, the seed crystals are zeolite Beta crystals, preferably zeolite Beta crystals which are obtainable or have preferably been obtained according to the synthetic method.

According to the synthetic method, any suitable amount of seed crystals can be provided in the mixture according to step (1), provided that a zeolitic material having a BEA framework structure is crystallized in step (2). In general, the amount of seed crystals contained in the mixture according to step (1) ranges from 0.1 to 50 wt.-% based on 100 wt.-% of $YO_2$ in the one or more sources for $YO_2$, preferably from 0.5 to 40 wt.-%, more preferably from 1 to 35 wt.-%, more preferably from 2 to 25 wt.-%, more preferably from 3 to 20 wt.-%, more preferably from 5 to 15 wt.-%, and even more preferably from 8 to 12 wt.-%.

In step (1) according to the synthetic method, the mixture can be prepared by any conceivable means, wherein mixing by agitation is preferred, preferably by means of stirring.

In one or more embodiments of the synthetic method, the mixture according to step (1) further comprises a solvent. Any conceivable solvent can be used in any conceivable amount, provided that a zeolitic material having a BEA framework structure can be crystallized in step (2) of the synthetic method. In one or more embodiments, the solvent comprises water, wherein the $H_2O:YO_2$ molar ratio of the mixture ranges from 1 to 100, preferably from 2 to 60, more preferably from 5 to 50, more preferably from 7 to 45, more preferably from 10 to 30, and particularly preferably from 15 to 25. According to the synthetic method, the $H_2O:YO_2$ molar ratio of the mixture ranges from 15 to 45, more preferably from 20 to 40, and even more preferably from 25 to 35. In specific embodiments, the solvent provided in step (1) is distilled water.

In general, the single components for providing the mixture of step (1) of the synthetic method can be added in any order, provided that a zeolitic material having a BEA framework structure is crystallized from the mixture in step (2) of the synthetic method. This may, for example, involve the addition of the optional solvent and optionally the one or more sources for $X_2O_3$ and/or the one or more sources for $OH^-$, followed by the addition of the one or more sources for $YO_2$, wherein the seed crystals are only added to the mixture afterwards. Alternatively, the addition of the optional solvent and optionally the one or more sources for $X_2O_3$ and/or the one or more sources for $OH^-$ may be first followed by the addition of the seed crystals, wherein the one or more sources for $YO_2$ is only added thereafter.

In general, step (2) according to the synthetic method can be conducted in any conceivable manner, provided that a zeolitic material having a BEA framework structure is crystallized from the mixture according to step (1). The mixture can be crystallized in any type of vessel, wherein a means of agitation is optionally employed, said agitation being preferably achieved by rotation of the vessel and/or stirring, and more preferably by stirring the mixture.

According to the synthetic method, the mixture is heated during at least a portion of the crystallization process in step (2). In general, the mixture can be heated to any conceivable temperature of crystallization, provided that a zeolitic material having a BEA framework structure is crystallized from the mixture. In one or more embodiments, the mixture is heated to a temperature of crystallization ranging from 80 to 200° C., more preferably from 90 to 180° C., more preferably from 95 to 170° C., more preferably from 100 to 160° C., more preferably from 110 to 150° C., and even more preferably from 115 to 145° C.

The heating in step (2) of the synthetic method can be conducted in any conceivable manner suitable for the crystallization of a zeolitic material having a BEA framework structure. In general, heating may be conducted at one temperature of crystallization or vary between different temperatures. In one or more embodiments, a heat ramp is used for reaching the temperature of crystallization, wherein, by way of example, the heating rate may range from 10 to 100° C./h, more preferably from 20 to 70° C./h, more preferably from 25 to 60° C./h, more preferably from 30 to 50° C./h, and even more preferably from 35 to 45° C./h.

In one or more embodiments of the synthetic method, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000 or of from 97,000 to 104,000 or of from 98,000 to 103,000 or of from 99,000 to 102,000 Pa.

In one or more embodiments of the synthetic method wherein a solvent is present in the mixture according to step (1), heating in step (2) is conducted under solvothermal conditions, meaning that the mixture is crystallized under autogenous pressure of the solvent which is used, for example by conducting heating in an autoclave or other crystallization vessel suited for generating solvothermal conditions. In specific embodiments wherein the solvent comprises or consists of water, preferably of distilled water, heating in step (2) is accordingly preferably conducted under hydrothermal conditions.

The apparatus which can be used in the synthetic method for crystallization is not particularly restricted, provided that the desired parameters for the crystallization process can be realized, in particular with respect to the one or more embodiments requiring particular crystallization conditions. In the one or more embodiments conducted under solvothermal conditions, any type of autoclave or digestion vessel can be used, wherein a Teflon-lined apparatus is preferred.

In general, the duration of the crystallization process in step (2) of the synthetic method is not particularly limited. In one or more embodiments involving heating of the mixture according to step (1), said crystallization process is conducted for a period ranging from 10 to 200 h, more preferably from 30 to 150 h, more preferably from 100 to 140 h, and even more preferably from 110 to 130 h. According to the synthetic method, crystallization is conducted for a period ranging from 5 to 100, 10 to 80 h, more preferably from 20 to 70 h, more preferably from 30 to 60 h, more preferably from 40 to 55 h, and even more preferably from 45 to 50 h.

According to one or more embodiments of the synthetic method, wherein the mixture is heated in step (2), said heating may be conducted during the entire crystallization process or during only one or more portions thereof, provided that a zeolitic material having the BEA framework structure is crystallized. In one or more embodiments, heating is conducted during the entire duration of crystallization.

In general, the process of the synthetic method can optionally comprise further steps for the work-up and/or further physical and/or chemical transformation of the zeolitic material having a BEA framework structure crystallized in step (2) from the mixture provided in step (1). The crystallized material can for example be subject to any sequence of isolation and/or washing procedures, wherein the zeolitic material obtained from crystallization in step (2) is preferably subject to one or more isolation and one or more washing procedures.

Isolation of the crystallized product can be achieved by any conceivable means. In one or more embodiments, isolation of the crystallized product can be achieved by means of filtration, ultrafiltration, diafiltration, centrifugation and/or decantation methods, wherein filtration methods can involve suction and/or pressure filtration steps.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and one or more alcohols, such as water and methanol or water and ethanol or water and propanol or water and methanol and ethanol or water and methanol and propanol or water and ethanol and propanol or water and methanol and ethanol and propanol. Water or a mixture of water and one or more alcohols, preferably water and ethanol, is preferred, distilled water being very particularly preferred as the only washing agent.

In one or more embodiments, the separated zeolitic material is washed until the pH of the washing agent, preferably the washwater, is in the range of from 6 to 8, preferably from 6.5 to 7.5, as determined via a standard glass electrode.

Furthermore, the synthetic method can optionally comprise one or more drying steps. In general, any conceivable means of drying can be used. Drying procedures preferably include heating and/or applying vacuum to the zeolitic material having a BEA framework structure. In envisaged embodiments of the synthetic method, one or more drying steps may involve spray drying, preferably spray granulation of the zeolitic material.

In embodiments which comprise one or more drying steps, the drying temperatures are preferably in the range of from 25° C. to 150° C., more preferably of from 60 to 140° C., more preferably of from 70 to 130° C. and even more preferably in the range of from 75 to 125° C. The durations of drying are preferably in the range of from 2 to 60 h, more preferably in the range of 6 to 48 hours, and even more preferably of from 12 to 24 h.

According to the synthetic method, the zeolitic material crystallized in step (2) can optionally be subject to one or more ion-exchange procedures. In general, any conceivable ion-exchange procedure with all possible ionic elements and/or molecules can be conducted on the zeolitic material. In one or more embodiments, as ionic elements one or more cation and/or cationic elements are employed which preferably comprise one or more cations and/or cationic elements selected from the group consisting of $H^+$, $NH_4^+$, lithium, potassium, calcium, magnesium, barium, transition metals, and combinations thereof, more preferably from the group consisting of $H^+$, $NH_4^+$, lithium, potassium, calcium, magnesium, barium, lanthanum, cerium, nickel, platinum, palladium, and combinations thereof, wherein even more preferably the one or more cation and/or cationic elements comprise $H^+$ and/or $NH_4^+$, preferably H.

In general, the optional washing and/or isolation and/or ion-exchange procedures comprised in the synthetic method can be conducted in any conceivably order and repeated as often as desired.

Therefore, according to specific embodiments, the synthetic method optionally comprises one or more of the following steps of (3) isolating the zeolitic material having a BEA framework structure, preferably by filtration, and/or (4) washing the zeolitic material having a BEA framework structure, and/or (5) drying the zeolitic material having a BEA framework structure, and/or (6) subjecting the zeolitic material having a BEA framework structure to an ion-exchange procedure, wherein the steps (3) and/or (4) and/or (5) and/or (6) can be conducted in any order, and wherein one or more of said steps is preferably repeated at least once.

In one or more embodiments, the synthetic method comprises one or more steps of isolating the zeolitic material crystallized according to step (2), more preferably by filtration thereof. According to the synthetic method, after the one or more steps of isolating, the zeolitic material is subject to one or more steps of drying, wherein more preferably the zeolitic material is subject to one or more steps of washing prior to the one or more drying steps. In a specific embodiment, the zeolitic material crystallized according to step (2) is subject to one or more steps of isolating, followed by one or more steps of washing, followed by one or more steps of drying.

According to a further embodiment of the synthetic method, the zeolitic material crystallized in step (2) is directly subject to one or more steps of drying, preferably to spray drying and or spray granulation, without isolating, washing, or drying of the zeolitic material beforehand. Directly subjecting the mixture obtained from step (2) of the synthetic method to a spray drying or spray granulation stage has the advantage that isolation and drying is performed in a single stage.

According to a further embodiment of the synthetic method, the zeolitic material obtained from crystallization in step (2) is subject to one or more isolating steps prior to being subject to one or more ion-exchange procedures, preferably to one or more isolating steps followed by one or more washing steps, and more preferably to one or more isolating steps followed by one or more washing steps followed by one or more drying steps.

The synthetic method does not comprise a calcination step generally involving the heating of the zeolitic material crystallized according to step (2) above a temperature of 500° C. More preferably, the synthetic method for the production of a zeolitic material having a BEA framework structure which does not comprise a calcination step refers to synthetic methods, wherein the zeolitic material crystallized according to step (2) is not subject to a temperature exceeding 450° C., more preferably 350° C., more preferably 300° C., more preferably 250° C., more preferably 200° C., and even more preferably 150° C. According to the synthetic method, after completion of step (2) of the synthetic method, wherein the crystallized zeolitic material is at ambient temperature, said material is subsequently not subject to any heating process.

Thus, according to the present invention, the one or more zeolitic materials provided as a catalyst in step (a) of the inventive process are preferably obtainable, and even more preferably obtained according to one or more of the aforementioned preferred and particularly synthetic methods.

As regards the one or more alkylatable organic compounds with which the catalyst is contacted in step (b) of the inventive process, there is no particular restriction as to the type of organic compounds which may be used as the one or more alkylatable compounds, provided that it may be alkylated with the one or more alkylating agents employed in said step. In this respect, it is noted that within the meaning of the present invention, the one or more alkylated organic compounds obtained in step (b) comprise one or more alkylated organic compounds which are the alkylation product of the reaction of one or more alkylatable organic compounds with one or more alkylating agents. Thus, in principle, the alkylatable organic compound may be any organic compound capable of reacting with at least one of the one or more alkylating agents used in step (b), wherein during the course of the reaction at least one covalent bond is formed between an atom of the alkylatable organic compound and a carbon atom of one or more of the one or more alkylating agents. As to the type of covalent bond which is formed between the alkylatable organic compound and the alkylating agent, there is again no particular restriction. Thus, in function of the valence of the one or more atoms of the alkylatable organic compound which forms a covalent bond with a carbon atom of the one or more alkylating agents, one or more single, double, and/or triple bonds may be formed, wherein preferably one or more single and/or double bonds are formed. According to the inventive process one or more single bonds are formed between one or more atoms of the alkylatable organic compound and one or more carbon atoms of the one or more alkylating agents.

According to one or more embodiments of the inventive process, the one or more alkylatable organic compounds comprise one or more aromatic compounds. In principle, there is no particular restriction as to the aromatic compounds which are employed as alkylatable organic compound according to the inventive process, provided that the aromatic compound may be alkylated with the one or more alkylating agents employed in step (b). Thus, by way of example, the aromatic compounds used in step (b) may contain mononuclear aromatic ring and/or polynuclear condensed aromatic ring moieties, wherein preferably the aromatic compound comprises one or more mononuclear aromatic ring moieties, and even more preferably one aromatic ring moiety. According to specific embodiments of the present invention, the aromaticity of the aromatic compound is due to the presence of one or more mononuclear aromatic rings contained therein, and even more preferably due to the presence of a single mononuclear aromatic ring contained therein. Regarding the one or more aromatic ring moieties contained in the aromatic compounds, there is no general restriction as to the type and number of ring members contained therein. Thus, by way of example, the one or more aromatic rings contained in the aromatic compounds may contain anywhere from 3 to 8 ring members, wherein, preferably, the aromatic ring contains from 4 to 7 ring members, and more preferably from 5 to 7 ring members. According to a specific embodiment, the one or more aromatic rings contained in the aromatic compounds contain 5 and/or 6 ring members, preferably 6 ring members. According to specific embodiments, the aromatic compounds comprise one or more condensed and/or uncondensed, and preferably uncondensed, 6-membered aromatic rings, and even more preferably one 6-membered aromatic ring.

There is no particular restriction according to the present invention as to the types of atoms contained as ring members of the aromatic compounds, provided that the aromatic compound is suitable for being alkylated by one or more of the one or more alkylating agents employed in step (b). Thus, by way of example, the ring members may be selected from the group consisting of carbon, nitrogen, oxygen, sulfur, and combinations of two or more thereof, preferably from the group consisting of carbon, nitrogen, oxygen, and combinations of two or more thereof. According to specific embodiments, the ring members of the aromatic compounds are carbon and/or nitrogen, and preferably carbon. With respect to the one or more compounds which may be used as the aromatic compounds, these may by way of example be selected from the group consisting of furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinazoline, pyridazine, cinnoline, benzene, naphthalene, anthracene, naphthacene, perylene, coronene, phenanthrene, and (further) heteroaromatic derivatives thereof. According to one or more embodiments of the present invention, the aromatic compounds comprise one or more compounds selected from the group consisting of benzene, naphthalene, and heteroaromatic derivatives thereof, more preferably from the group consisting of benzene and heteroaromatic derivatives thereof, wherein even more preferably the one or more alkylatable aromatic compounds comprise benzene.

According to the present invention, the aromatic compounds comprised among the one or more alkylatable organic compounds may be substituted with one or more functional groups. In principle, according to the present invention there is no particular restriction as to the number or type of functional groups which may be present in the aromatic compounds, provided that the aromatic compound is suitable for being alkylated with one or more of the alkylating agents provided in step (b). Thus, by way of example, the functional group may comprise one or more functional groups selected from the group consisting of OH, halides, OR, $NH_2$, NHR, NRR', substituted and unsubstituted cyclic, linear, or branched alkyl, substituted and unsubstituted acyl, substituted or unsubstituted ester, and combinations of two or more thereof, wherein R and R' independently stand for substituted or unsubstituted alkyl which may respectively be cyclic, linear, or branched. According to one or more embodiments, the one or more functional groups comprise one or more functional groups selected from the group consisting of OH, F, Cl, OR, $NH_2$, NHR, NRR', substituted and unsubstituted alkyl, substituted and unsubstituted acyl, substituted or unsubstituted ester, and combinations of two or more thereof, more preferably, one or more functional groups selected from the group consisting of OH, F, Cl, OR, NHR, NRR', substituted and unsubstituted alkyl, substituted and unsubstituted acyl, and combinations of two or more thereof, more preferably one or more functional groups selected from the group consisting of OH, F, Cl, OR, NHR, NRR', substituted and unsubstituted alkyl, substituted and unsubstituted acyl, and combinations of two or more thereof, more preferably one or more functional groups selected from the group consisting of OH, OR, substituted and unsubstituted alkyl, substituted and unsubstituted acyl, and combinations of two or more thereof, wherein even more preferably the one or more functional group comprises substituted and/or unsubstituted alkyl, preferably unsubstituted alkyl, wherein independently from one another alkyl, R, and/or R' preferably stands for ($C_1$ to $C_6$)alkyl, more preferably ($C_1$ to $C_4$)alkyl, more preferably ($C_1$ to $C_3$)alkyl, more preferably ($C_1$ or $C_2$)alkyl, wherein even more preferably the one or more functional groups comprises $C_1$-alkyl, wherein substituted and/or unsubstituted methyl, and particularly unsubstituted methyl is particularly preferred.

As to the amount of functional groups with which the aromatic compounds may be substituted, by way of example their number may range anywhere from 1 to 10, wherein preferably the aromatic compounds are substituted with from 1 to 5 functional groups, more preferably with from 1 to 4, more preferably with from 1 to 3, more preferably with 1 or 2, and even more preferably with 1 functional group.

Thus, by way of example, regarding specific embodiments of the inventive process wherein one or more substituted aromatic compounds are employed as one or more of the one or more alkylatable organic compounds, one or more compounds may suitably be used which are selected from the group consisting of toluene, xylene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, 4-ethyl-m-xylene, dimethylnaphthalene, ethylnaphthalene, 2,3-dimethylanthracene, 9-ethylanthracene, 2-methylanthracene, o-methylanthracene, 9,10-dimethylphenanthrene, and 3-methyl-phenanthrene. According to specific embodiments of the inventive process employing one or more alkyl substituted aromatic compounds as preferred alkylatable organic compounds, said compounds include one or more compounds selected from the group consisting of toluene, xylene, normal propylbenzene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene, 1,2,3,4-tetraethylbenzene, 1,2,3,5-tetramethylbenzene, 1,2,4-triethylbenzene, 1,2,3-trimethylbenzene, m-butyltoluene, p-butyltoluene, 3,5-diethyltoluene, o-ethyltoluene, p-ethyltoluene, m-propyltoluene, and 4-ethyl-m-xylene, more preferably from the group consisting of toluene, normal propylbenzene, ethylbenzene, cumene, butylbenzene, isoamylbenzene, and isohexylbenzene, more preferably from the group consisting of toluene, normal propylbenzene, ethylbenzene, and cumene, wherein even more preferably the one or more alkylatable organic compounds comprise toluene and/or ethylbenzene, and particularly preferably toluene.

Thus, according specific embodiments of the present invention, one or more of the one or more alkylatable compounds are selected from the group consisting of benzene substituted with ($C_1$ to $C_3$)alkyl, more preferably with ($C_1$ or $C_2$)alkyl, more preferably with $C_1$-alkyl, wherein substituted and/or unsubstituted methyl, and particularly unsubstituted methyl is particularly preferred, such that the one or more alkylatable aromatic compounds comprise toluene.

Therefore, according to one or more embodiments of the inventive process, the alkylatable organic compounds comprises one or more alkylatable aromatic compounds, preferably one or more compounds selected from the group consisting of mono- and polynuclear aromatic and heteroaromatic compounds, wherein one or more of the one or more alkylatable aromatic compounds is optionally substituted with one or more functional groups.

According to specific embodiments, the one or more alkylatable aromatic compounds comprises one or more aromatic compounds selected from the group consisting of substituted or unsubstituted benzene, naphthalene, anthracene, naphthacene, perylene, coronene, phenanthrene, and heteroaromatic derivatives thereof, preferably from the group consisting of substituted or unsubstituted benzene, naphthalene, and heteroaromatic derivatives thereof, more preferably from the group consisting of substituted or unsubstituted benzene and heteroaromatic derivatives thereof, wherein more preferably the one or more alkylatable aromatic compounds comprise substituted and/or unsubstituted benzene, and even more preferably benzene.

Furthermore, according to specific embodiments wherein the one or more alkylatable aromatic compounds are optionally substituted with one or more functional groups, it is particularly preferred that the one or more functional groups comprise one or more functionalities selected from the group consisting of linear or branched alkyl, aryl, alkaryl, alkoxy, aryloxy, cycloalkyl, halide, and derivatives thereof, more preferably from the group consisting of linear or branched alkyl, alkoxy, cycloalkyl, halide, and derivatives thereof, more preferably from the group consisting of linear or branched alkyl, alkoxy, halide, and derivatives thereof, more preferably from the group consisting of linear or branched alkyl, halide, and derivatives thereof, wherein even more preferably the one or more functional groups comprise one or more linear or branched alkyl groups and/or derivatives thereof, preferably one or more linear or branched alkyl groups, and even more preferably one or more linear alkyl groups, wherein alkyl is preferably $C_1$ to $C_5$ alkyl, more preferably $C_1$ to $C_4$ alkyl, more preferably $C_1$ to $C_3$ alkyl, more preferably methyl or ethyl, and wherein even more preferably the functional group is methyl.

With respect to the actual alkylation of the alkylatable compound in step (b) of the inventive process, there is no particular restriction as to the position or positions at which the one or more alkylatable organic compounds are alkylated, provided that one or more covalent bonds are formed between the one or more alkylatable organic compounds and a carbon atom of one or more of the one or more alkylating agents. According to one or more embodiments of the present invention wherein the one or more alkylatable organic compounds comprise one or more aromatic compounds, any position of the aromatic compound may in principle be alkylated, such that the one or more condensed and/or uncondensed aromatic rings contained in the aromatic compound may be alkylated and/or one or more of the one or more functional groups contained in one or more of the aromatic compounds may equally or alternatively be alkylated in step (b). In instances wherein one or more of the aromatic rings are alkylated it is generally preferred that the one or more members of the aromatic ring subject to the alkylation are members which are not optionally functionalized, and in particular which contain one or more hydrogen atoms which in step (b) are respectively substituted by one or more alkylating agents.

According to a specific embodiment, one or more to the one or more condensed and/or uncondensed aromatic rings are alkylated in step (b) of the inventive process, wherein in principle any one or more of the members of the one or more aromatic rings may by suitably alkylated. In instances wherein one or more members of the one or more aromatic rings are suitably alkylated, one or more carbon and/or nitrogen atom members atom members of the one or more aromatic rings is suitably alkylated, wherein it is preferred that one or more carbon atom members is suitably alkylated.

As concerns the one or more alkylating agents used in the inventive process, there is principally no restriction as to the type of compounds which may be used to this effect, provided that they may be suitably used to alkylate one or more of the one or more alkylatable organic compounds. Same applies accordingly with respect to the type of alkyl moiety contained in the alkylating agent such that in principle any substituted or unsubstituted cyclic, linear, or branched alkyl moiety may be contained therein, wherein the preferred and particularly preferred functional groups with which the alkyl moieties of the one or more alkylating agents may be substituted preferably comprise one or more functional groups selected among those defined in the foregoing with respect to the preferred alkylatable aromatic compounds. According to specific embodiments of the inventive process, the alkyl moiety is an unsubstituted and preferably linear and unbranched alkyl moiety.

Within the meaning of the present invention, the term "alkyl moiety" preferably refers to the moiety contained in the alkylating agent which is bound to one or more of the one or more alkylatable compounds during the alkylation reaction of the inventive process. Regarding the size of the alkyl moiety contained in the one or more alkylating agents, there is again no general restriction in this respect according to the inventive process, such that in principle any suitable alkyl moiety may be contained in the one or more alkylating agents, provided that said alkyl moiety may be covalently bound to one or more of the one or more alkylatable organic compound during the alkylation reaction in step (b) of the inventive process. Thus, by way of example, the size of the substituted or unsubstituted cyclic, linear, or branched alkyl moiety may be comprised in the range of from $C_1$ to $C_{22}$, wherein preferably it is comprised in the range of from $C_1$ to $C_{20}$, more preferably in the range of from $C_1$ to $C_{18}$, more preferably of from $C_1$ to $C_{16}$, more preferably of from $C_1$ to $C_{14}$, more preferably of from $C_1$ to $C_{10}$, more preferably of from $C_1$ to $C_8$, more preferably of from $C_1$ to $C_6$, more preferably of from $C_1$ to $C_5$, more preferably of from $C_1$ to $C_4$, more preferably of from $C_1$ to $C_3$, wherein even more preferably the alkyl moiety is a $C_1$ or $C_2$ alkyl moiety, and particularly preferably a $C_2$ alkyl moiety.

By way of example, regarding the one or more alkylating agents used in step (b) of the inventive process, one or more compounds may be comprised therein which are selected from the group consisting of olefins such as ethylene, propylene, as well as linear and branched butenes and pentenes; alcohols (including monoalcohols, dialcohols and trialcohols) such as methanol, ethanol, as well as linear and branched propanols, butanols, and pentanols; aldehydes such as formaldehyde, acetaldehyde, propionaldehyde, butyraldehyde, and n-valeraldehyde; and alkyl halides such as methyl chloride, ethyl chloride, as well as linear and branched propyl chlorides, butyl chlorides, and pentyl chlorides.

Therefore, according to one or more embodiments of the inventive process, the one or more alkylating agents comprise one or more compounds selected from the group consisting of olefins, alcohols, aldehydes, alkyl halides, and derivatives thereof, preferably one or more compounds selected from the group consisting of olefins, alcohols, alkyl halides, and derivatives thereof, more preferably one or more compounds selected from the group consisting of olefins, alcohols, and derivatives thereof, wherein even more preferably the one or more alkylating agents comprise one or more compounds selected from the group consisting of olefins, and derivatives thereof.

Regarding specific embodiments of the present invention wherein the one or more alkylating agents comprise one or more olefins, there is no particular restriction as to the olefins which may be used provided that one or more of the alkylatable organic compounds may be alkylated in step (b) of the inventive process. Thus, in principle, any conceivable number of double bonds may be present therein, wherein preferably 1 to 4 double bonds are contained therein, more preferably 1 to 3 double bonds, and even more preferably 1 or 2 double bonds are contained therein. According to specific embodiments the one or more alkylating agents comprise one or more olefins containing one single double bond. Furthermore, regarding the size of the olefin preferably comprised among the one or more alkylating agents, there is again no particular restriction, provided that it is suitable for alkylating one or more of the one or more alkylatable organic compounds in step (b) of the inventive process. Thus, by way of example, the olefin may have anywhere from 2 to 22 carbon atoms, wherein it preferably has from 2 to 20 carbon atoms, more preferably from 2 to 18 carbon atoms, more preferably from 2 to 16 carbon atoms, preferably from 2 to 14 carbon atoms, preferably from 2 to 10 carbon atoms, preferably from 2 to 8 carbon atoms, preferably from 2 to 6 carbon atoms, preferably from 2 to 5 carbon atoms, preferably from 2 to 4 carbon atoms, and wherein even more preferably the olefins comprised in the one or more alkylating agents have 2 and/or 3 carbon atoms. Furthermore, there is also no particular restriction with respect to the structure of the olefin preferably comprised in the one or more alkylating agents, provided that it is suitable for alkylating one or more of the one or more alkylatable organic compounds. Thus, the olefin may be linear or branched, wherein a portion of the branched olefins and the linear olefins as such may be cyclic. According to specific embodiments, the one or more alkylating agents comprise one or more linear and unbranched olefins, wherein said olefins are preferably non-cyclic.

Furthermore, the one or more olefins comprised in the one or more alkylating agents may be optionally substituted with one or more functional groups. In principal the olefins which may be used in the inventive process are not particularly restricted with respect to the type or number of functional groups they may have, provided that one or more of the one or more alkylatable organic compounds may be alkylated using said olefin in step (b) of the inventive process. In one or more embodiments, the one or more functional groups with which the olefins are optionally substituted preferably comprise one or more functional groups selected among those defined with defined in the foregoing with respect to the preferred alkylatable aromatic compounds. According to specific embodiments of the inventive process, however, the one or more alkylating agents preferably comprise one or more unsubstituted olefins.

Therefore, According to specific embodiments of the inventive process, the one or more alkylating agents comprise one or more alkenes, more preferably one or more alkenes selected from the group consisting of ethene, propene, butene, preferably linear butenes, pentene, preferably linear pentenes, and derivatives thereof, more preferably from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more alkylating agents comprise ethene and/or derivatives thereof, preferably ethene.

According to certain embodiments of the present invention, the alkylating agents comprise mixtures of light olefins. According to said embodiments, there is no particular restriction as to the type and composition of such mixtures provided that one or more of the one or more alkylatable organic compounds may be suitably alkylated, wherein by way of example mixtures of ethylene, propylene, (linear and/or branched) butenes, and/or (linear and/or branched) pentenes. Such mixtures may be provided from any conceivable source wherein by way of example such mixtures may be obtained from refinery streams such as for example from fuel gas, gas plant off-gas such as off-gas containing ethylene and/or propylene, and naphtha cracker off-gas such as off-gas containing light olefins such as for example mixtures comprising ethane, ethylene, propane, propylene, isobutane, n-butane, (linear and/or branched) butene, and/or (linear and/or branched) pentanes, and refinery FCC streams comprising propane and propylene.

As concerns the compounds which are contacted in step (b) of the inventive process for the alkylation reaction, there is no particular restriction according to the present invention neither as to the choice of the one or more alkylatable organic compounds in view of the one or more alkylating agents which are used therein nor, vice versa, as to the choice of the one or more alkylating agents in view of the one or more alkylatable organic compounds which are used therein, provided that one or more of the one or more alkylating agents used therein is capable of alkylating one or more of the one or more alkylatable organic compounds in the presence of the catalyst comprising the one or more zeolitic materials. According to one or more embodiments of the inventive process, the one or more alkylatable organic compounds comprise one or more organic compounds selected from the group consisting of substituted or unsubstituted benzene, toluene, and heteroaromatic derivatives thereof, and the one or more alkylating agents comprise one or more olefins selected from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more olefins comprise ethene and/or derivatives thereof, and preferably ethene. According to embodiments of the inventive process which are further preferred, the one or more alkylatable organic compounds comprise one or more organic compounds selected from the group consisting of benzene, toluene, and heteroaromatic derivatives thereof, and the one or more alkylating agents comprise one or more olefins selected from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more olefins comprise ethene and/or derivatives thereof, and preferably ethene. According to specific embodiments of the inventive process, the one or more alkylatable organic compounds comprise one or more organic compounds selected from the group consisting of benzene and/or toluene, wherein even more preferably the one or more alkylatable organic compounds comprise benzene, and the one or more alkylating agents comprise one or more olefins selected from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more olefins comprise ethene and/or derivatives thereof, and preferably ethene.

Therefore, According to specific embodiments of the present invention, the one or more alkylatable organic compounds comprise one or more organic compounds selected from the group consisting of substituted or unsubstituted benzene, toluene, and heteroaromatic derivatives thereof, preferably from the group consisting of benzene, toluene, and heteroaromatic derivatives thereof, wherein more preferably the one or more alkylatable organic compounds comprise benzene and/or toluene, preferably benzene, and wherein the one or more alkylating agents comprise one or more olefins selected from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more olefins comprise ethene and/or derivatives thereof, and preferably ethene.

Concerning the alkylation reaction conducted in step (b) of the inventive process, there is no particular restriction according to the present invention as to the respective amounts and proportions of the one or more alkylatable organic compounds and the one or more alkylating agents which may be used therein, nor to particular restrictions exist with respect to the reaction conditions and parameters, provided that these are suitable for allowing the reaction of one or more of the one or more alkylatable organic compounds with one or more of the one or more alkylating agents in the presence of the catalyst comprising the one or more zeolitic materials. Thus, regarding the temperatures employed in one or more of the one or more reactors in step (b), these may by way of example range anywhere from 0 to 500° C. In instances in which two or more reactors are employed in step (b), the temperatures employed in the individual reactors may be the same or may differ from one another. According to one or more embodiments, the temperature employed in one or more of the one or more reactors ranges from 100 to 350° C., more preferably from 130 to 300° C., more preferably from 150 to 250° C., and even more preferably from 160 to 190° C. According to specific embodiments, the temperature used in one or more of the one or more reactors ranges from 165 to 175° C.

Therefore, according to one or more embodiments of the inventive process step (b) is conducted at a temperature ranging from 100 to 350° C., preferably from 100 to 350° C., more preferably from 130 to 300° C., more preferably from 150 to 250° C., more preferably from 160 to 190° C., and even more preferably from 165 to 175° C.

Furthermore, as concerns the pressure under which the alkylation reaction in step (b) of the inventive process is conducted, there is again no particular restriction in this respect provided that the pressure which is employed in the one or more reactors is suitable for conducting alkylation. As with respect to the temperature, in instances wherein two or more reactors are employed, the pressure used in the reactors may be the same or different. Thus, by way of example, the pressure in one or more of the one or more reactors may be comprised in the range of anywhere from 0.2 to 250 bar, wherein preferably the pressure in one or more of the reactors is comprised in the range of from 0.5 to 200 bar, more preferably of from 1 to 150 bar, more preferably of from 3 to 120 bar, more preferably from 5 to 100 bar, more preferably from more preferably of from 10 to 80 bar, more preferably of from 15 to 70 bar, more preferably of from 25 to 60 bar, wherein even more preferably the pressure in one or more of the reactors is comprised in the range of from 30 to 55 bar.

Accordingly, according to one or more embodiments of the inventive process, step (b) is conducted at a pressure comprised in the range of from 0.2 to 250 bar, preferably of from 0.5 to 200 bar, more preferably of from 1 to 150 bar, more preferably of from 3 to 120 bar, more preferably of from 5 to 100 bar, more preferably of from 10 to 80 bar, more preferably of from 15 to 70 bar, more preferably of from 25 to 60 bar, and even more preferably of from 30 to 55 bar.

According to the inventive process, the alkylation reaction is generally conducted such that the organic reactants, i.e., the one or more alkylatable organic compounds and the one or more alkylating agents, are brought into contact with an alkylation catalyst in a suitable reaction zone such in one or more of the respective one or more reactors. In this respect, there is no general restriction as to the reaction mode provided that it is suitable for obtaining one or more alkylated compounds. Accordingly, the inventive process may principally be conducted as a batch reaction, or as a continuous process, or as a combination of batch reaction and continuous process.

According to one or more embodiments of the present invention wherein the inventive process is conducted as a batch reaction, in addition to the reaction parameters outlined in the foregoing and below, there is no particular limitation as to the reaction time which is employed provided that one or more alkylated organic compounds may be obtained in step (b). Thus, by way of example, the duration of the batch reaction may be comprised in the range of from 0.5 to 100 h, wherein preferably the batch reaction is conducted for a duration ranging from 1 to 80 h, more preferably from 5 to 60 h, more preferably from 10 to 40 h, more preferably from 15 to 35 h, more preferably from 20 to 28 h, and even more preferably from 22 to 26 h.

Therefore, according to one or more embodiments of the present invention, and according to specific embodiments wherein the inventive process is conducted as a batch reaction, step (b) is conducted for a duration of from 0.5 to 100 h, preferably of from 1 to 80 h, more preferably of from 5 to 60 h, more preferably of from 10 to 40 h, more preferably of from 15 to 35 h, more preferably of from 20 to 28 h, and even more preferably of from 22 to 26 h.

According to specific embodiments of the present invention, the inventive process is conducted in a continuous mode. According to said specific embodiments there is no particular restriction as to the state of the catalyst comprising the one or more zeolitic materials, such that by way of example a fixed bed or a fluidized bed technology may be employed, in addition to a combination of fixed and fluidized bed technologies, wherein in instances in which both fixed and fluidized bed technologies are employed, two or more reactors are preferably employed in step (b), wherein the fixed and fluidized bed technologies are preferably confined to separate reactors, respectively. According to specific embodiments employing a continuous mode, in one or more of the one or more reactors the catalyst of the inventive process is maintained as a fixed bed.

Furthermore, according to specific embodiments of the present invention wherein the inventive process is conducted as a continuous reaction, in addition to the reaction parameters outlined in the foregoing and below, there is no particular limitation as to the feed weight hourly space velocity (WHSV) which is employed in one or more of the one or more reactors used in the continuous process, provided that one or more alkylated organic compounds may be obtained in step (b). Thus, by way of example, the WHSV employed in one or more of the one or more reactors may be comprised anywhere in the range of from 0.1 to 500 $h^{-1}$, wherein the WHSV is preferably comprised in the range of from 0.5 and 100 $h^{-1}$, more preferably of from 0.1 to 20 $h^{-1}$, and even more preferably of from 1 to 6 $h^{-1}$.

Thus, according to one or more embodiments of the present invention, step (b) of the inventive process is carried out as a continuous process.

Furthermore, according to a specific embodiment of the present invention, the one or more reactors employed in step (b) contain the catalyst in the form of a fixed bed and/or as a fluidized bed, wherein preferably one or more of the one or more reactors contain the catalyst in the form of a fixed bed.

Thus, various types of reactors may be used in the inventive process. For example, the process may be carried out in batchwise fashion by adding the catalyst and alkylatable organic compound feedstock to a stirred autoclave, heating to a suitable reaction temperature, and then adding alkylating agent feedstock. A heat transfer fluid may be circulated through the jacket of the autoclave, or a condenser may be provided, to remove the heat of reaction and maintain a constant temperature. The process also may be performed in a catalytic distillation mode.

Further by way of example, for large scale industrial processes a fixed bed reactor operating in an upflow or downflow mode or a moving bed reactor operating with concurrent or countercurrent catalyst and hydrocarbon flows may be employed. These reactors may contain a single catalyst bed or multiple catalyst beds and may be equipped for the interstage addition of the one or more alkylating agents as well as interstage cooling. Interstage addition of the one or more alkylating agents and/or isothermal operation may be used to enhance product quality and catalyst life. Furthermore, a moving bed reactor may be used for enabling continuous removal of spent catalyst for regeneration and replacement by fresh or regenerated catalysts.

As concerns the proportions in which the one or more alkylatable organic compounds and the one or more alkylating agents are used, there is no particular limitation according to the present invention provided that one or more alkylated organic compounds are obtained in step (b). According to specific embodiments of the inventive process, at least an equimolar amount of the one or more alkylatable organic compounds is employed, wherein preferably a molar excess of the one or more alkylatable organic compounds is used realtive to the amount of the one or more alkylating agents. Thus by way of example, according to one or more embodiments of the inventive process, the molar ratio of the one or more alkylatable organic compounds to the one or more alkylating agents is comprised in the range of from 0.1:1 to 50:1, and preferably of from 0.5:1 to 10:1. According to specific embodiments, the molar ratio is comprised in the range of from 1:1 to 30:1, more preferably of from 1:1 to 10:1, more preferably of from 1:1 to 5:1, and even more preferably of from 1:1 to 2:1.

Therefore, according to one or more embodiments of the present invention, the molar ratio of the one or more alkylatable organic compounds to the one or more alkylating agents employed in step (b) ranges from 0.1:1 to 50:1, preferably from 0.5:1 to 10:1, more preferably from 1:1 to 30:1, more preferably from 1:1 to 10:1, more preferably from 1:1 to 5:1, and even more preferably from 1:1 to 2:1.

According to the present invention the catalyst provided in step (a) may in principle be used in any suitable form, provided that it is capable of catalyzing the alkylation reaction. Thus, the alkylation catalyst provided in step (a) which comprises one or more zeolitic materials having a BEA framework structure can be employed as such, such as by way of example in the form of a powder, a spray powder or a spray granulate.

When the inventive process is employed on an industrial scale, it is however preferable not to employ the alkylation catalyst comprising the zeolitic material as powder or sprayed material but rather in the form of a molding.

Therefore, according to one or more embodiments of the inventive process, the catalyst comprising one or more zeolitic materials having a BEA framework structure is provided in the form of a molding.

In general, the powder or sprayed material can be shaped to form a molding without any other compounds, such as for example by suitable compacting, to obtain moldings of a desired geometry, such as in the form of tablets, cylinders, and/or spheres. The molding may however comprise all conceivable further compounds in addition to the one or more zeolitic materials comprised in the catalyst, provided that it is ensured that the resulting molding is capable of catalyzing the alkylation reaction in step (b). According to one or more embodiments, at least one suitable binder material is used in the production of the molding. In the context of this embodiment, a mixture of the catalyst comprising one or more zeolitic materials and the one or more binders is prepared. Suitable binders are in general all compounds which impart adhesion and/or cohesion between the one or more zeolitic materials which are to be bound, in particular beyond the physisorption which may be present without a binder. Examples of such binders are metal oxides, such as $SiO_2$, $Al_2O_3$, $TiO_2$, $ZrO_2$ or $MgO$, or clays or mixtures of two or more of these compounds. As $Al_2O_3$ binders, clay minerals and naturally occurring or synthetic aluminas, for example alpha-, beta-, gamma-, delta-, eta-, kappa-, chi- or theta-alumina and the inorganic or organometallic precursor compounds thereof, such as gibbsite, bayerite, boehmite, pseudoboehmite or trialkoxyaluminates, such as aluminum triisopropylate are preferred in particular. Further preferred binders are amphiphilic compounds having a polar and a nonpolar moiety, and graphite. Further binders are, for example, clays, such as montmorillonites, kaolins, bentonites, halloysites, dickites, nacrites or anaxites.

According to the present invention, the binders can be used as such for the production of a molding. In the context of the present invention, it is however also possible to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate. In the context of the present invention, binders which either completely or partly consist of $SiO_2$ or are a precursor of $SiO_2$, from which $SiO_2$ is formed in at least one further step in the production of the moldings are to be mentioned. In this context, both colloidal silica and "wet process" silica as well as "dry process" silica can be used. These are very particularly preferably amorphous silica, the size of the silica particles being, for example, in the range of from 5 to 100 nm and the surface of the silica particles being in the range of from 50 to 500 $m^2/g$. Colloidal silica, preferably in the form of an alkaline and/or ammoniacal solution, more preferably in the form of an ammoniacal solution, is, for example, commercially available as, inter alia, Ludox®, Syton®, Nalco® or Snowtex®. "Wet process" silica is, for example, commercially available, inter alia, as Hi-Sil®, Ultrasil®, Vulcasil®, Santocel®, Valron-Estersil®, Tokusil® or Nipsil®. "Dry process" silica is, for example, commercially available, inter alia, as Aerosil®, Reolosil®, Cab-O-Sil®, Fransil® or Arc-Silica®. The binders are preferably used in an amount which leads to the finally resulting moldings whose binder content is up to 80% by weight, more preferably in the range of from 5 to 80% by weight, more preferably in the range of from 10 to 70% by weight, more preferably in the range of from 10 to 60% by weight, more preferably in the range of from 15 to 50% by weight, more preferably in the range of from 15 to 45% by weight, particularly preferably in the range of from 15 to 40% by weight, based in each case on the total weight of the finally resulting molding.

In principle, the molding comprising the alkylation catalyst of the present invention may be obtained according to any suitable procedure, provided that the molding may catalyze the alkylation in step (b) of the inventive process. According to one or more embodiments of the present invention, the molding is obtainable and preferably obtained according to a process for the production of a molding comprising the steps of (I) preparing of a mixture containing the alkylation catalyst comprising the one or more zeolitic materials, and optionally at least one binder;

(II) optionally kneading of the mixture;

(III) molding of the kneaded mixture to give at least one molding;

(IV) optionally drying of the at least one molding; and/or (V) optionally calcining of the at least one dried molding.

The term "finally resulting molding" as used in the context of the present invention relates to a molding as obtainable and preferably obtained from the optional drying and/or calcining steps (IV) and/or (V), particularly preferably as obtainable and preferably obtained from step (IV).

Therefore, the mixture of binder or precursor of a binder and the catalyst comprising one or more zeolitic materials can be mixed with at least one further compound for further processing and for the formation of a plastic material. Here, inter alia, pore formers may preferably be mentioned. In the process of the present invention, all compounds which, with regard to the finished molding, provide a certain pore size and/or a certain pore size distribution and/or certain pore volumes can be used as pore formers. In one or more embodiments, the pore formers use in the process of the present invention are polymers which are dispersible, suspendable or emulsifiable in water or in aqueous solvent mixtures. Preferred polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugars or natural fibers. Further suitable pore formers are, for example, pulp or graphite. If pore formers are used in the preparation of the mixture according to (I), the pore former content, preferably the polymer content of the mixture according to (I) is preferably in the range of from 5 to 90% by weight, preferably in the range of from 15 to 75% by weight, and particularly preferably in the range of from 25 to 55% by weight, based in each case on the amount of the one or more zeolitic materials in the mixture according to (I). If desired for the pore size distribution to be achieved, a mixture of two or more pore formers may also be used. In an embodiment of the process of the present invention, the pore formers are removed in a step (V) by calcination to give the porous molding. According to a specific embodiment of the present invention, however, the molding obtained in step (III) is subsequently not subject to a calcination step. With respect to the calcination of the molding preferably used in the inventive process, the term "calcination" refers to a calcination step as defined in the foregoing with respect to the one or more zeolitic materials. Therefore, According to specific embodiments of the present invention wherein the molding obtained in step (III) is subsequently not subject to a calcination step, it is accordingly preferred according to said embodiments either not to employ a pore former or, alternatively, to use one or more pore formers which may be suitably removed either by a heating step which is not a calcination step within the meaning of the present invention and/or which may be removed by other means than by suitable heating of the preferred molding containing one or more pore formers.

In the context of a likewise specific embodiment of the present invention, at least one pasting agent is added in the preparation of the mixture according to (I). Pasting agents which may be used are all compounds suitable for this purpose. These are preferably organic, in particular hydrophilic polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene or polytetrahydrofuran. Accordingly, particular compounds which also act as pore formers can be used as pasting agents. In a specific embodiment of the process of the present invention as described below, these pasting agents are removed in a step (V) by calcination to give the porous molding. According to the present invention, however, it is particularly preferred that the molding obtained in step (III) is subsequently not subject to a calcination step. Therefore, According to specific embodiments of the present invention wherein the molding obtained in step (III) is subsequently not subject to a calcination step, it is accordingly preferred according to said embodiments either not to employ a pasting agent or, alternatively, to use one or more pasting agents which may be suitably removed either by a heating step which is not a calcination step within the meaning of the present invention and/or which may be removed by other means than by suitable heating of the preferred molding containing one or more pasting agents.

According to a further embodiment of the present invention, at least one acidic additive may added during the preparation of the mixture according to (I). In this respect organic acidic compounds are preferred which can be removed in an optional calcination step (V). Carboxylic acids, for example formic acid, oxalic acid and/or citric acid, are particularly preferred. It is also possible to use two or more of these acidic compounds. As for the aforementioned pore formers and pasting agents, however, it is preferred to use one or more acidic additives and preferably one or more organic acidic compounds which may be removed either by a heating step which is not a calcination step within the meaning of the present invention and/or which may be removed by other means than by suitable heating of the preferred molding containing one or more acidic additives, preferably one or more organic acidic compounds.

The order of addition of the components of the mixture according to (I) which contains the alkylation catalyst comprising the one or more zeolitic materials having a BEA framework structure is not critical. In particular is both possible first to add the at least one binder, then the at least one pore former and the at least one acidic compound and finally the at least one pasting agent and to interchange the sequence with regard to the at least one binder, the at least one pore former, the at least one acidic compound and the at least one pasting agent.

After the addition of the binder to the alkylation catalyst comprising the zeolitic materials to which, if appropriate, at least one of the compounds described above have already been added, the mixture according to (I) is normally homogenized for from 10 to 180 minutes. Inter alia, kneaders, edge mills or extruders are particularly preferably used for the homogenization. The mixture is preferably kneaded. On the industrial scale, treatment in an edge mill is preferably employed for the homogenization. The homogenization is carried out as a rule at temperatures in the range of from about 10° C. to the boiling point of the pasting agent and normal pressure or slightly superatmospheric pressure. Thereafter, if appropriate, at least one of the compounds described above can be added. The mixture thus obtained is homogenized, preferably kneaded, until an extrudable plastic material has formed.

According to the process of the present invention for the production of a molding, the homogenized mixture is subsequently molded. In the context of the present invention, those processes in which the molding is effected by extrusion in conventional extruders, for example to give extrudates having a diameter of preferably from 1 to 10 mm, particularly preferably from 2 to 5 mm, are preferred for the shaping processes. Such extrusion apparatuses are described, for example, in Ullmann's Enzyklopädie der Technischen Chemie, 4th Edition, Vol. 2, page 295 et seq., 1972. In addition to the use of a screw-type extruder, a plunger-type extruder is also preferably used for the molding. In principle, however, all known and/or suitable kneading and molding apparatuses and processes may be used for the shaping. Examples of these are inter alia: briquetting, i.e. mechanical compression with or without addition of additional binder material; pelleting, i.e. compacting by circular and/or rotational movements; sintering, i.e. the material to be molded is subjected to a thermal treatment. The shape of the moldings produced according to the invention can be chosen as desired. In particular, inter alia spheres, oval shapes, cylinders or tablets are possible.

In the context of the present invention, step (III) is preferably followed by at least one drying step. In principle, any suitable drying step may be used, provided that a dry molding is provided. According to the present invention, the drying step does not involve temperatures used in a calcination step within the meaning of the present invention.

In the context of the present invention, an optional drying step (IV) is optionally followed by at least one calcination step (V). According to certain embodiments, a calcination step (V) is directly carried out after the molding step (III). According to the present invention, the molding containing the alkylation catalyst comprising the one or more zeolitic materials having the BEA framework structure is not subject to a calcination step (V) subsequently to the optional drying step (IV), wherein according to said specific embodiments not involving a calcination step (V) it is preferred that the production process comprises one or more drying steps (IV) subsequently to the molding step (III).

According to embodiments wherein the molding is obtainable and preferably obtained according to the aforementioned method for the production of a molding which comprises one or more calcination steps (V), the calcination may be generally carried out at any temperature as defined within the meaning of the present invention, wherein it is preferably carried out at temperatures in the range of from 300 to 700° C., and more preferably from 400 to 600° C. According to said embodiments, the calcination can be effected under any suitable gas atmosphere, air and/or lean air being preferred. Furthermore, the calcination is preferably carried out in a muffle furnace, a rotary kiln and/or a belt calcination oven. It is possible for the temperatures during a calcination step to remain constant or to be changed continuously or discontinuously. If calcination is effected twice or more often, the calcination temperatures can be different or identical in the individual steps.

Before and/or after the optional drying step (IV) and/or before and/or after the optional calcination step (V), the at least one molding can, if appropriate, be treated with a concentrated or dilute Broenstedt acid or a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, such as nitrilotriacetic acid, sulfosalicylic acid or ethylenediaminetetraacetic acid. If appropriate, this at least one treatment with at least one Broenstedt acid is followed by at least one drying step (IV) and/or at least one calcination step (V).

According to a further embodiment of the process of the present invention, the moldings preferably provided in step (a) and used in step (b) can, for better hardening, be subject to a water steam treatment, after which preferably drying is effected at least once again and/or calcination is effected at least once again. For example, after at least one drying step and at least one subsequent calcination step, the calcined molding is subjected to the steam treatment and is then dried at least once again and/or calcined at least once again.

Furthermore, the present invention further relates to the use of a catalyst comprising one or more zeolitic materials as employed in step (a) of the inventive process according to the embodiments and specific embodiments of the present invention in an alkylation reaction. In particular, the inventive use concerns the use of an catalyst having one or more zeolitic materials having a BEA framework structure, wherein the one or more zeolitic materials are obtainable from a synthetic process which does not employ an organotemplate as structure directing agent, in an alkylation reaction. According to one or more embodiments of the inventive use, the catalyst used in the alkylation reaction corresponds to the catalyst provided in step (a) of the inventive process according to the embodiments and specific embodiments of the present invention.

In principle, according to the present invention, the inventive use of the catalyst comprising one or more zeolitic materials having a BEA framework structure is not limited to any particular types of alkylation reactions, provided that the reaction of one or more alkylatable compounds with one or more alkylating agents may be suitably catalyzed by the catalyst. Thus, there is no particular restriction as to the alkylatable compounds which are employed in such a reaction, nor as to the alkylating agents used therein, provided that the use of the catalyst allows for the production of one or more alkylated compounds. According to one or more embodiments of the inventive use, the one or more alkylatable compounds and the one or more alkylating agents respectively correspond to preferred and particularly preferred alkylatable organic compounds and/or, preferably and, to preferred and particularly preferred alkylating agents used in the inventive process for the alkylation of an organic compound. Furthermore, according to further embodiments, the catalyst comprising one or more zeolitic materials of the inventive use is preferably a catalyst which corresponds to the catalyst used in the inventive process for the alkylation of an organic compound.

Therefore, the present invention also relates to the use of a catalyst comprising one or more zeolitic materials having a BEA framework structure in an alkylation reaction including one or more alkylatable organic compounds and one or more alkylating agents as the reagents, wherein the one or more zeolitic materials is obtainable from a synthetic process which does not employ an organotemplate as structure directing agent.

The present invention includes the following embodiments, wherein these include the specific combinations of embodiments as indicated by the respective interdependencies defined therein:

1. A process for the alkylation of an organic compound comprising:
   (a) providing a catalyst comprising one or more zeolitic materials having a BEA framework structure, wherein the BEA framework structure comprises $YO_2$ and optionally comprises $X_2O_3$, wherein Y is a tetravalent element, and X is a trivalent element,
   (b) contacting the catalyst with one or more alkylatable organic compounds in the presence of one or more alkylating agents in one or more reactors for obtaining one or more alkylated organic compounds, wherein the one or more zeolitic materials is obtainable from a synthetic process which does not employ an organotemplate as structure directing agent.
2. The process of embodiment 1, wherein one or more zeolitic materials are non-calcined.
3. The process of embodiment 1 or 2, wherein Y is selected from the group consisting of Si, Sn, Ti, Zr, Ge, and combinations of two or more thereof, Y preferably being Si.
4. The process of any of embodiments 1 to 3, wherein X is selected from the group consisting of Al, B, In, Ga, and combinations of two or more thereof, X preferably being Al.
5. The process of any of embodiments 1 to 4, wherein the Y:X molar ratio of one or more of the one or more zeolitic materials is in the range of from 1 to 50, preferably of from 2 to 35, more preferably of from 2.5 to 25, more preferably of from 3 to 15, more preferably of from 3.5 to 10, more preferably of from 4 to 8, and even more preferably in the range of from 4 to 6.
6. The process of any of embodiments 1 to 5, wherein one or more of the one or more zeolitic materials comprises one or more alkali metals M, preferably one or more alkali metals M selected from the group consisting of Li, Na, and K, wherein more preferably the one or more alkali metals M comprise Na and/or K, more preferably Na, and wherein even more preferably M is Na.
7. The process of c embodiment 6, wherein the molar ratio of M:X ranges from 0.01 to 20, preferably from 0.05 to 10, more preferably from 0.1 to 5, more preferably from 0.5 to 2, more preferably from 0.7 to 1.5, more preferably from 0.9 to 1.3, more preferably from 1 to 1.2, and even more preferably from 1 to 1.1.
8. The process of embodiment 6 or 7, wherein at least a portion of the alkali metal atoms M is substituted by one or more cations and/or cationic elements, wherein the one or more cations and/or cationic elements preferably comprise one or more cations and/or cationic elements selected from the group consisting of $H^+$, $NH_4^+$, lithium, potassium, calcium, magnesium, barium, transition metals, and combinations thereof, more preferably from the group consisting of $H^+$, $NH_4^+$, lithium, potassium, calcium, magnesium, barium, lanthanum, cerium, nickel, platinum, palladium, and combinations thereof, wherein even more preferably at least a portion of the alkali metal atoms M is exchanged with $H^+$ and/or $NH_4^+$, preferably with $H^+$, wherein the substituted catalyst is preferably obtainable by ion-exchange.

9. The process of any of embodiments 1 to 8, wherein one or more of the one or more zeolitic materials has an X-ray diffraction pattern comprising at least the following reflections:

| Intensity (%) | Diffraction angle 2θ/° [Cu K(alpha 1)] |
| --- | --- |
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern.

10. The process of embodiment 9, wherein the X-ray diffraction pattern comprises the following reflection:

| Intensity (%) | Diffraction angle 2θ/° [Cu K(alpha 1)] |
| --- | --- |
| [6-26] | [25.54-25.74] |

11. The process of any of embodiments 1 to 10, wherein the BET surface area determined according to DIN 66135 of one or more of the one or more zeolitic materials ranges from 150 to 650 $m^2/g$, preferably from 200 to 550 $m^2/g$, more preferably from 230 to 500 $m^2/g$, more preferably from 250 to 450 $m^2/g$, more preferably from 270 to 400 $m^2/g$, more preferably from 280 to 340 $m^2/g$, and even more preferably from 290 to 320 $m^2/g$.

12. The process of any of embodiments 1 to 11, wherein the one or more zeolitic materials comprise zeolite Beta.

13. The process of any of embodiments 1 to 12, wherein the one or more alkylatable organic compounds comprises one or more alkylatable aromatic compounds, preferably one or more compounds selected from the group consisting of mono- and polynuclear aromatic and heteroaromatic compounds, wherein one or more of the one or more alkylatable aromatic compounds is optionally substituted with one or more functional groups.

14. The process of embodiment 3, wherein the one or more alkylatable aromatic compounds comprises one or more aromatic compounds selected from the group consisting of substituted or unsubstituted benzene, naphthalene, anthracene, naphthacene, perylene, coronene, phenanthrene, and heteroaromatic derivatives thereof, preferably from the group consisting of substituted or unsubstituted benzene, naphthalene, and heteroaromatic derivatives thereof, more preferably from the group consisting of substituted or unsubstituted benzene and heteroaromatic derivatives thereof, wherein more preferably the one or more alkylatable aromatic compounds comprise substituted and/or unsubstituted benzene, and even more preferably benzene.

15. The process of embodiment 13 or 14, wherein the one or more functional groups comprise one or more functionalities selected from the group consisting of linear or branched alkyl, aryl, alkaryl, alkoxy, aryloxy, cycloalkyl, halide, and derivatives thereof, more preferably from the group consisting of linear or branched alkyl, alkoxy, cycloalkyl, halide, and derivatives thereof, more preferably from the group consisting of linear or branched alkyl, alkoxy, halide, and derivatives thereof, more preferably from the group consisting of linear or branched alkyl, halide, and derivatives thereof, wherein even more preferably the one or more functional groups comprise one or more linear or branched alkyl groups and/or derivatives thereof, preferably one or more linear or branched alkyl groups, and even more preferably one or more linear alkyl groups, wherein alkyl is preferably $C_1$ to $C_5$ alkyl, more preferably $C_1$ to $C_4$ alkyl, more preferably $C_1$ to $C_3$ alkyl, more preferably methyl or ethyl, and wherein even more preferably the functional group is methyl.

16. The process of any of embodiments 1 to 15, wherein the one or more alkylating agents comprise one or more compounds selected from the group consisting of olefins, alcohols, aldehydes, alkyl halides, and derivatives thereof, preferably one or more compounds selected from the group consisting of olefins, alcohols, alkyl halides, and derivatives thereof, more preferably one or more compounds selected from the group consisting of olefins, alcohols, and derivatives thereof, wherein even more preferably the one or more alkylating agents comprise one or more compounds selected from the group consisting of olefins, and derivatives thereof.

17. The process of embodiment 16, wherein the olefins comprise one or more alkenes, more preferably one or more alkenes selected from the group consisting of ethene, propene, butene, preferably linear butenes, pentene, preferably linear pentenes, and derivatives thereof, more preferably from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the olefins comprise ethene and/or derivatives thereof, preferably ethene.

18. The process of any of embodiments 1 to 17, wherein the one or more alkylatable organic compounds comprise one or more organic compounds selected from the group consisting of substituted or unsubstituted benzene, toluene, and heteroaromatic derivatives thereof, preferably from the group consisting of benzene, toluene, and heteroaromatic derivatives thereof, wherein more preferably the one or more alkylatable organic compounds comprise benzene and/or toluene, preferably benzene, and wherein the one or more alkylating agents comprises one or more olefins selected from the group consisting of ethene, propene, butene, preferably linear butenes, and derivatives thereof, more preferably from the group consisting of ethene, propene, 2-butene, preferably trans-2-butene, and derivatives thereof, more preferably from the group consisting of ethene, propene, and derivatives thereof, and wherein even more preferably the one or more olefins comprise ethene and/or derivatives thereof, and preferably ethene.

19. The process of any of embodiments 1 to 18, wherein the molar ratio of the one or more alkylatable organic compounds to the one or more alkylating agents ranges from 0.1:1 to 50:1, preferably from 0.5:1 to 10:1, more preferably from 1:1 to 30:1, more preferably from 1:1 to 10:1, more preferably from 1:1 to 5:1, and even more preferably from 1:1 to 2:1.
20. The process of any of embodiments 1 to 19, wherein step (b) is conducted at a temperature ranging from 100 to 350° C., preferably from 130 to 300° C., more preferably from 150 to 250° C., more preferably from 160 to 190° C., and even more preferably from 165 to 175° C.
21. The process of any of embodiments 1 to 20, wherein step (b) is conducted at a pressure comprised in the range of from 0.2 to 250 bar, preferably of from 0.5 to 200 bar, more preferably of from 1 to 150 bar, more preferably of from 3 to 120 bar, more preferably of from 5 to 100 bar, more preferably of from 10 to 80 bar, more preferably of from 15 to 70 bar, more preferably of from 25 to 60 bar, and even more preferably of from 30 to 55 bar.
22. The process of any of embodiments 1 to 21, wherein step (b) is conducted for a duration of from 0.5 to 100 h, preferably of from 1 to 80 h, more preferably of from 5 to 60 h, more preferably of from 10 to 40 h, more preferably of from 15 to 35 h, more preferably of from 20 to 28 h, and even more preferably of from 22 to 26 h.
23. The process of any of embodiments 1 to 22, wherein the process is a continuous process.
24. The process of any of embodiments 1 to 23, wherein the one or more reactors contain the catalyst in the form of a fixed bed and/or as a fluidized bed, wherein preferably one or more of the one or more reactors contain the catalyst in the form of a fixed bed.
25. The process of any of embodiments 1 to 24, wherein the catalyst comprising one or more zeolitic materials having a BEA framework structure is provided in the form of a molding.
26. Use of a catalyst comprising one or more zeolitic materials having a BEA framework structure in an alkylation reaction including one or more alkylatable organic compounds and one or more alkylating agents as the reagents, wherein the one or more zeolitic materials are obtainable from a synthetic process which does not employ an organotemplate as structure directing agent.

BRIEF DESCRIPTION OF THE FIGURES

FIG. 1 further includes the respective line patterns of zeolite Beta obtained from template mediated synthesis, of zeolite P, and of mordenite for comparison.

FIG. 2 further includes the respective line patterns of zeolite Beta obtained from template mediated synthesis and of mordenite for comparison.

EXAMPLES

Example 1

2.31 g of $NaAlO_2$ and 1.09 g of NaOH were dissolved in 79.2 g of $H_2O$, followed by addition of 0.9 g of Al-beta zeolite seed crystals (CP814C zeolite Beta from Zeolyst International). 112.6 g of sodium-water glass solution (26 wt.-% $SiO_2$ and 8 wt.-% $Na_2O$ from Fa. Woellner) were then slowly added to the mixture, wherein after adding 10-20 g of the sodium-water glass solution a clear gel is produced which is then dissolved after further addition of the solution.

The mixture was then transferred into an autoclave and crystallized at 120° C. for 120 h. After having let the reaction mixture cool to room temperature, it was filtered and the solid residue repeatedly washed with distilled water, after which it was dried at 120° C. for 16 h thus affording 6.5 g of a white crystalline product. The product displayed a crystallinity grade of 74% compared to the Al-beta zeolite used in synthesis.

Elemental analysis of the crystalline product of Example 1 afforded Na:Si:Al molar ratios of 1.1:4.3:1.

Figure 1A:
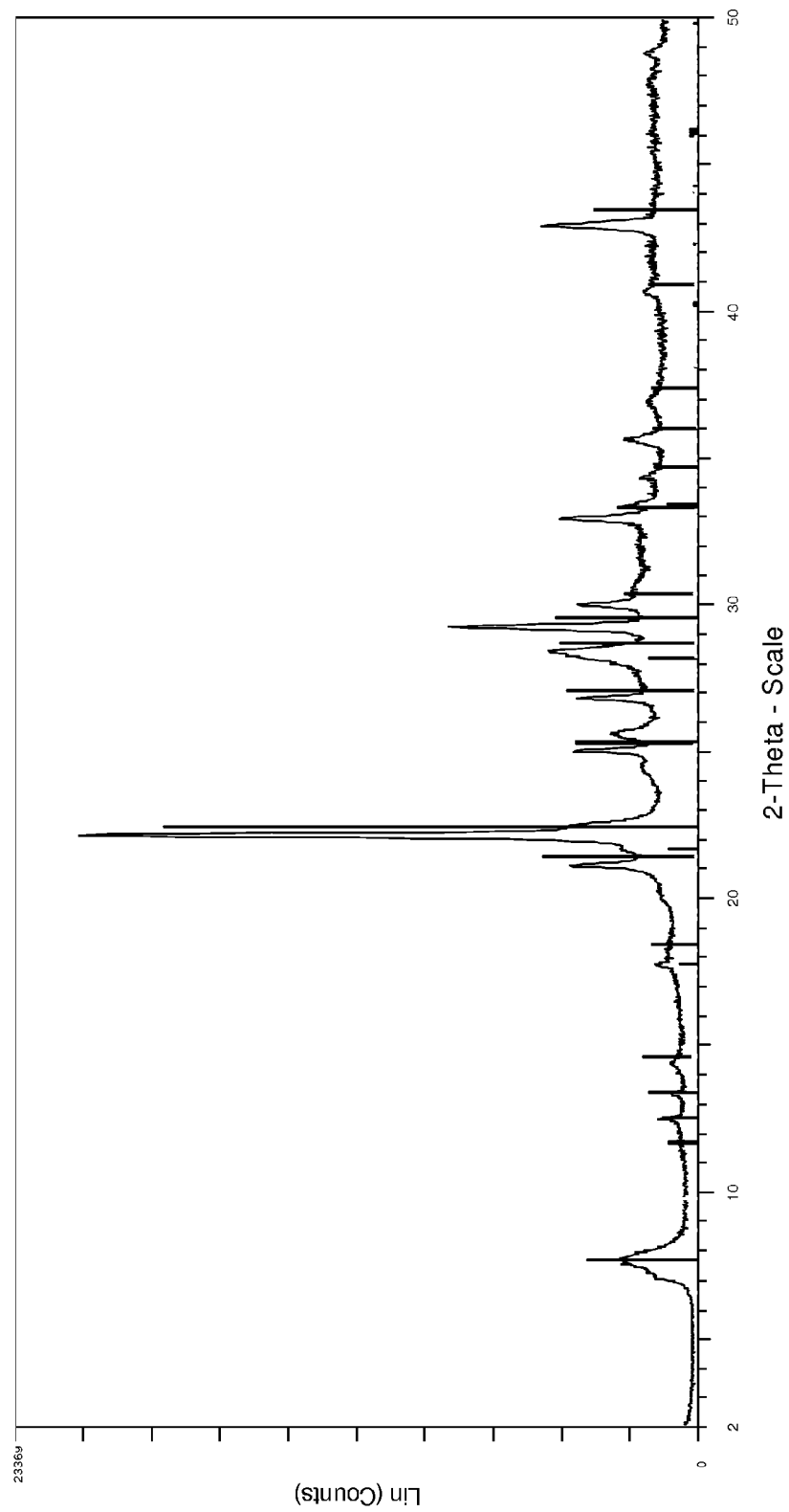
FIG. 1a shows the X-ray diffraction (XRD) pattern (measured using Cu K alpha-1 radiation) of the zeolitic material obtained from organotemplate-free synthesis according to Example 1. In the figure, the diffraction angle 2 theta in ° is shown along the abscissa and the intensities are plotted along the ordinate.

In FIG. 1a, the XRD of the crystalline product obtained from the organotemplate-free synthesis of Example 1 after filtration and drying is displayed. In particular, the XRD pattern is typical for a BEA framework structure.

Figure 1B:
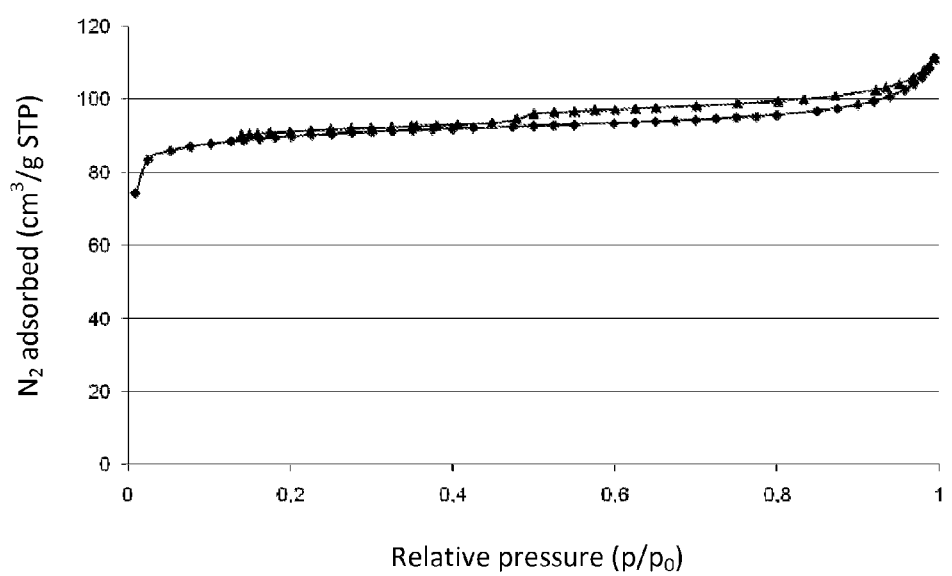
FIG. 1b shows the nitrogen adsorption isotherm according to Example 1. In the figure, the relative pressure $p/p^0$ is plotted along the abscissa and the pore volume in $cm^3/g$ STP (standard pressure and temperature), determined according to DIN 66134 at 77 K, is plotted along the ordinate. The values for the adsorption are indicated by the symbols (♦) and the values for the desorption are indicated by the symbols (▲).

In FIG. 1b, the nitrogen isotherm obtained using the crystalline product of Example 1 is shown. In particular, the step-like curve of a type I adsorption isotherm typical of microporous solids is evident (cf. DIN 66135), indicating that the as-synthesized zeolitic material has open micropores. The evaluation of the data gave an equivalent surface of 397.49 $m^2/g$ according to the Langmuir method, and a BET surface area of 303.71 $m^2/g$.

Example 2

1.34 g of $NaAlO_2$ and 6.54 g of NaOH were dissolved in 142.2 g of $H_2O$, followed by addition of 1.69 g of Al-beta zeolite seed crystals (CP814C zeolite Beta from Zeolyst International) and 16.9 g of fumed silica (Aerosil® 200) while stirring. The mixture was then transferred into an autoclave and crystallized at 140° C. for 48 h. After having let the reaction mixture cool to room temperature, it was filtered and the solid residue repeatedly washed with distilled water, after which it was dried at 120° C. for 16 h thus affording 5.3 g of a white crystalline product. The product displayed a crystallinity grade of 68% compared to the Al-beta zeolite used in synthesis.

Elemental analysis of the crystalline product of Example 1 afforded Na:Si:Al molar ratios of 1.05:5.2:1.

Figure 2:
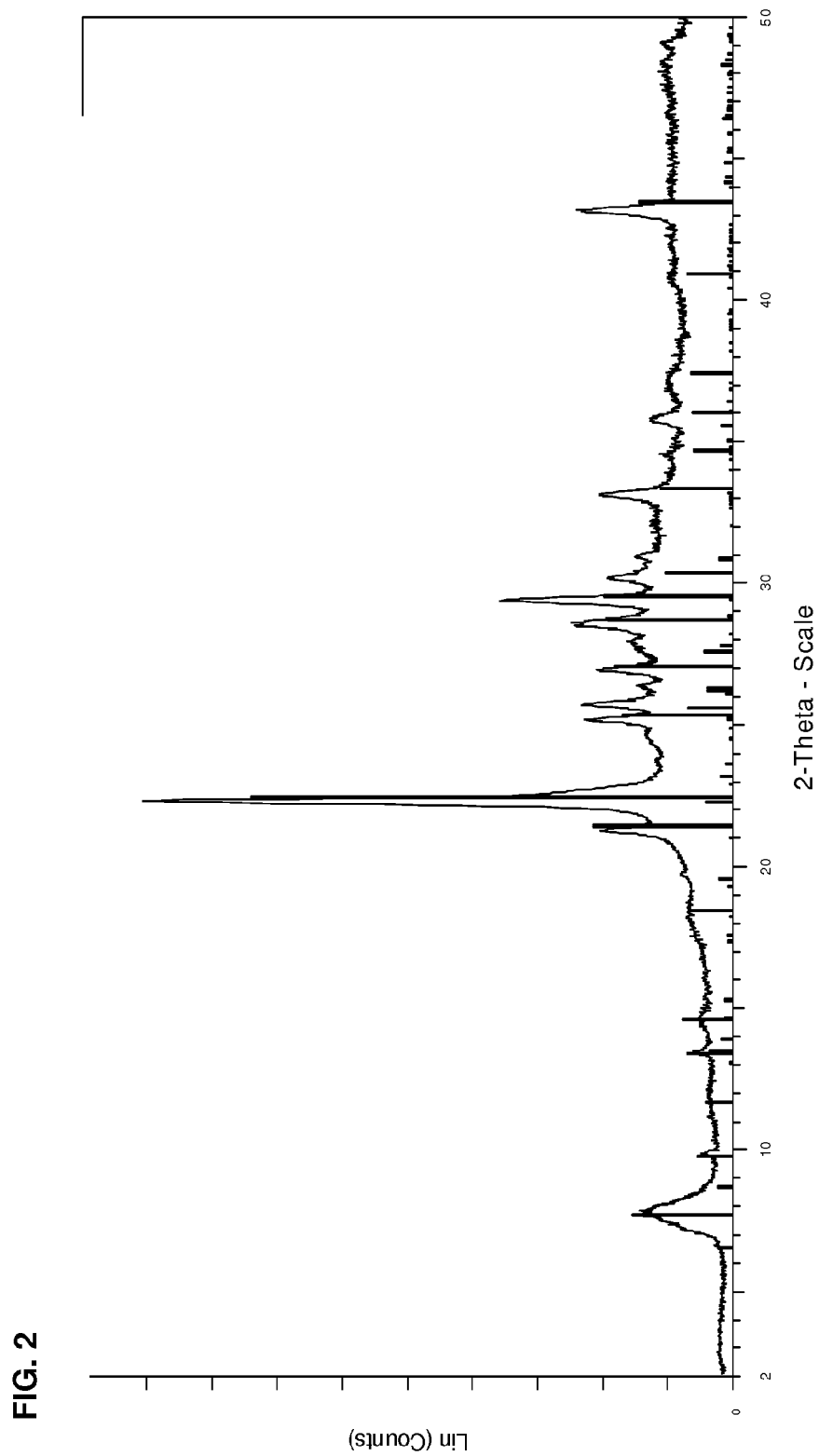
FIG. 2 shows the X-ray diffraction (XRD) pattern (measured using Cu K alpha-1 radiation) of the zeolitic material obtained from organotemplate-free synthesis according to Example 2. In the figure, the diffraction angle 2 theta in ° is shown along the abscissa and the intensities are plotted along the ordinate.

In FIG. 2, the XRD of the crystalline product obtained from the organotemplate-free synthesis of Example 2 after filtration and drying is displayed. In particular, the XRD pattern is typical for a BEA framework structure.

Example 3

Alkylation of Benzene with Ethene 125 mg of zeolite Beta obtained from Example 2 were placed in a reaction vessel, after which it was presaturated with ethene (5 bar) during 0.5 h at room temperature. 20 ml of benzene were then added to the reaction vessel, after which the vessel was heated at 170° C. for 24 h under stirring (1350 rpm).

The procedure was then repeated using a commercial zeolite Beta (CP811-BL25 from PQ Corp.) displaying an Si/Al molar ratio of 10.8. The results from the analysis of the respective reaction mixtures thus obtained are shown in Table 1:

TABLE 1

Analysis of the reaction products from Example 3.

| zeolite | benzene conversion | selectivity with respect to ethene | | | |
|---|---|---|---|---|---|
| | | ethyl-benzene | diethyl-benzene | oligomers | other |
| Example 2 | 10.1% | 94.6% | 3.5% | 1.6% | 0.3% |
| commercial | 10.1% | 92.4% | 4.5% | 1.2% | 1.9% |

Thus, as may be taken from the results displayed in Table 1, compared to commercial zeolite Beta obtained from templated synthesis, the zeolite Beta obtained from an organotemplate-free synthetic procedure affords a higher selectivity towards the production of the monoalkylated product at the same conversion rate. More importantly, however, the selectivity towards the dialkylated product is significantly lower, in addition to other side-products which include triethylbenzenes. Accordingly, a clearly higher selectivity towards the monoalkylated product ethylbenzene is possible using a zeolite Beta obtained from organotemplate-free synthesis, in addition to a lower amount of di- and trialkylated products, thus affording a highly efficient process for the production of ethylbenzene.

Example 4

Alkylation of Toluene with Ethene

The procedure of Example 3 was repeated using toluene instead of benzene. Furthermore, the procedure was additionally conducted using the zeolite from Example 1. The results from the analysis of the respective reaction mixtures thus obtained are shown in Table 2:

TABLE 2

Analysis of the reaction products from Example 4 (reaction time: 24 h).

| zeolite | toluene conversion | selectivity with respect to ethene | | | | |
|---|---|---|---|---|---|---|
| | | ethyl-toluene | diethyl-toluene | butyl-toluene | oligomers | other |
| Example 1 | 9.0% | 93.8% | 3.3% | 0.3% | 2.3% | 0.4% |
| Example 2 | 12.0% | 92.1% | 4.7% | 0.2% | 1.9% | 0.2% |
| commercial | 12.8% | 82.7% | 8.9% | 0.3% | 0.6% | 7.6% |

Thus as may be taken from the results displayed in Table 2, the advantages demonstrated in Example 1 with respect to the ethylation of benzene are also observed for the ethylation of toluene under the same reaction conditions. In particular, despite a slightly lower conversion rate, the processes using zeolite Beta obtained from organotemplate-free synthesis afford a higher selectivity towards the production of the monoalkylated species, combined with lower selectivities towards the di- and trialkylated species. As may be noted in the present, the selectivity towards the production of oligomers is somewhat increased compared to using a commercial zeolite Beta as catalyst. However, this is far less of a disadvantage than the higher selectivities towards polyalkylated products observed using commercial zeolite Beta, in particular since their separation from the reaction mixture is far more time- and cost-intensive than the removal of oligomer side-products.

The procedure was then repeated, and the reaction was interrupted after 4.25 h. The results from the analysis of the respective reaction mixtures thus obtained are shown in Table 3:

TABLE 3

Analysis of the reaction products from Example 4 (reaction time: 4.25 h).

| zeolite | toluene conversion | selectivity with respect to ethene | | | | |
|---|---|---|---|---|---|---|
| | | ethyl-toluene | diethyl-toluene | butyl-toluene | oligomers | other |
| Example 1 | 3.5% | 85.9% | 1.0% | 1.3% | 8.2% | 3.6% |
| Example 2 | 6.5% | 91.2% | 2.4% | 0.2% | 3.3% | 2.9% |
| commercial | 7.6% | 92.7% | 5.7% | 0.3% | 0.1% | 1.2% |

As may be taken from the results in Table 3, a shorter reaction period affords a lower conversion rate for the zeolite Beta obtained from organotemplate-free synthesis compared to the commercial zeolite. Furthermore the selectivity towards the amount of oligomers and other side products such as trialkylated species and the like is increased. However, as for the results displayed in Table 2, it is again apparent that the selectivity towards the dialkylated product is greatly reduced compared to the values observed when using the commercial zeolite obtained from templated synthesis. In fact, compared to the results displayed in Table 2 for longer reaction times, the advantage in this respect is actually increased with respect to the process involving the use of a commercial zeolite Beta catalyst.

Accordingly, although the inventive process affords somewhat lower selectivities towards the monoalkylated product in addition to higher selectivities with respect to oligomers and other side-products when using shorter reaction times, the advantages with respect to the lower selectivity towards the monoalkylated products are further increased relative to the process using a commercial zeolite Beta obtained from templated synthesis. Accordingly, also for shorter reaction periods, the use of a zeolite Beta obtained from organotemplate-free synthesis remains highly advantageous, in particular with respect to the reduced selectivity towards the production of the dialkylated species.

What is claimed is:
1. A process for the alkylation of an organic compound comprising:
  (a) providing a catalyst comprising one or more zeolitic materials having a BEA framework structure, wherein the BEA framework structure comprises $YO_2$ and comprises $X_2O_3$, wherein Y is Si and X is Al,
  (b) contacting the catalyst with one or more alkylatable organic compounds in the presence of one or more alkylating agents in one or more reactors for obtaining one or more alkylated organic compounds, wherein a process for synthesizing the one or more zeolitic materials does not employ an organotemplate as a structure directing agent, and wherein the one or more alkylatable organic compounds comprises one or more aromatic compounds selected from the group consisting of substituted or unsubstituted benzene, naphthalene, anthracene, naphthacene, perylene, coronene, phenanthrene, and heteroaromatic derivatives thereof.

2. The process of claim 1, wherein the one or more zeolitic materials are non-calcined.

3. The process of claim 1, wherein the Y: X molar ratio of one or more of the one or more zeolitic materials is in the range of from 1 to 50.

4. The process of claim 1, wherein one or more of the one or more zeolitic materials comprises one or more alkali metals M.

5. The process of claim 4, wherein the molar ratio of M: X ranges from 0.01 to 20.

6. The process of claim 4, wherein at least a portion of the alkali metal atoms M is substituted by one or more cations and/or cationic elements.

7. The process of claim 1, wherein one or more of the one or more zeolitic materials has an X-ray diffraction pattern comprising at least the following reflections:

| Intensity (%) | Diffraction angle 2θ/° [Cu K(alpha 1)] |
|---|---|
| [9-29] | [21.06-21.26] |
| 100 | [22.11-22.31] |
| [10-30] | [25.01-25.21] |
| [8-28] | [26.77-26.97] |
| [12-32] | [28.38-28.58] |
| [27-47] | [29.22-29.42] |
| [7-27] | [29.99-30.19] |
| [9-29] | [32.85-33.25] |
| [11-31] | [42.86-43.26] | wherein 100% relates to the intensity of the maximum peak in the X-ray powder diffraction pattern.

8. The process of claim 7, wherein the X-ray diffraction pattern comprises the following reflection:

| Intensity (%) | Diffraction angle 2θ/° [Cu K(alpha 1)] |
|---|---|
| [6-26] | [25.54-25.74] |

9. The process of claim 1, wherein the BET surface area determined according to DIN 66135 of one or more of the one or more zeolitic materials ranges from 150 to 650 $m^2/g$.

10. The process of claim 1, wherein the one or more zeolitic materials comprise zeolite Beta.

11. The process of claim 1, wherein one or more of the one or more alkylatable organic compounds is substituted with one or more functional groups.

12. The process of claim 11, wherein the one or more functional groups comprise one or more functionalities selected from the group consisting of linear or branched alkyl, aryl, alkaryl, alkoxy, aryloxy, cycloalkyl, halide, and derivatives thereof.

13. The process of claim 1, wherein the one or more alkylating agents comprise one or more compounds selected from the group consisting of olefins, alcohols, aldehydes, alkyl halides, and derivatives thereof.

14. The process of claim 11, wherein the olefins comprise one or more alkenes.

15. The process of claim 1, wherein the one or more alkylating agents comprises one or more olefins selected from the group consisting of ethene, propene, butene, and derivatives thereof.

16. The process of claim 1, wherein the molar ratio of the one or more alkylatable organic compounds to the one or more alkylating agents ranges from 0.1:1 to 50:1.

17. The process of claim 1, wherein step (b) is conducted at a temperature ranging from 100 to 350° C.

18. The process of claim 1, wherein step (b) is conducted at a pressure in the range of from 0.2 to 250 bar.

19. The process of claim 1, wherein step (b) is conducted for a duration of from 0.5 to 100 h.

20. The process of claim 1, wherein the process is a continuous process.

21. The process of claim 1, wherein the one or more reactors contain the catalyst in the form of a fixed bed and/or as a fluidized bed.

22. The process of claim 1, wherein the catalyst comprising one or more zeolitic materials having a BEA framework structure is provided in the form of a molding.

* * * * *